United States Patent [19]
Clemence et al.

[11] Patent Number: 5,559,130
[45] Date of Patent: Sep. 24, 1996

[54] PYRROLIDINYL PYRIDONES FOR TREATING PAIN

[75] Inventors: François Clemence; Michel Fortin; Odile Le Martret, all of Paris, France

[73] Assignee: Roussel Uclaf, France

[21] Appl. No.: 346,017

[22] Filed: Nov. 29, 1994

Related U.S. Application Data

[62] Division of Ser. No. 56,241, Apr. 30, 1993, Pat. No. 5,395,843, which is a continuation of Ser. No. 598,545, Nov. 16, 1990, abandoned.

[30] Foreign Application Priority Data

Oct. 17, 1989 [FR] France .................... 89 13545

[51] Int. Cl.$^6$ .............. A61K 31/445; C07D 401/08
[52] U.S. Cl. .............. 514/326; 514/428; 540/597; 546/188; 548/567; 548/568
[58] Field of Search .............. 540/597; 546/188, 546/208; 548/568, 567; 514/326, 428

[56] References Cited

U.S. PATENT DOCUMENTS 3,058,986  10/1962  Lutz et al. ..................... 514/424
4,960,788  10/1990  Carenze et al. ................ 514/424

OTHER PUBLICATIONS

Lentia et al. "3–Amino–triiodoaminobenzoyl compounds for us as x–ray contrast agents" CA 56:5585d (1962).
Casini et al "N–diakylaminomethy and N–cycloalkyenimi-nomethy–ethyl–phenyl glutarimides" CA 60:7985f (1964).
Fleck et al. "Comparison of the biological efficiency of C and N Mannich bases . . . " CA 82:25657a (1975).
Malec et al. "Pharmacological properties of new derivatives of glutethimide" CA 84:12451v (1976).
Hook et al. "Synthesis of polyamine–linked bis daunmycin hydrozones and their interaction with DNA" CA 112:91218x (1990).
McOmie : "Protective groups in organic chemistry" Plenum Press, P. 43, 49, 52, 61 (1973).

Primary Examiner—Ceila Chang
Attorney, Agent, or Firm—Bierman & Muserlian

[57] ABSTRACT

A compound selected from the group consisting of all possible racemic, enantiomeric and diastereoisomeric forms of a compound of the formula

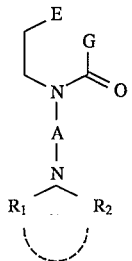

wherein E and G together form a group selected from the group:

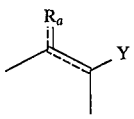

consisting of a)

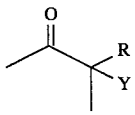

or, if appropriate, its tautomer

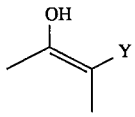

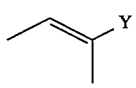

and

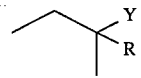

or E is —COOR$_3$ and G is

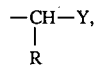

wherein A, Y, R, Ra, R$_1$ and R$_2$ are as defined in the specification.

10 Claims, No Drawings

PYRROLIDINYL PYRIDONES FOR TREATING PAIN

PRIOR APPLICATIONS

This is a division of U.S. patent application Ser. No. 056,241 filed Apr. 30, 1993, now U.S. Pat. No. 5,395,843 which is a continuation of U.S. patent application Ser. No. 598,545 filed Nov. 16, 1990, now abandoned.

STATE OF THE ART

Related prior art includes U.S. patent application Ser. Nos. 4,197,239 and 4,197,241.

OBJECTS OF THE INVENTION

It is an object of the invention to provide the novel compounds of formula I and their non-toxic, pharmaceutically acceptable acid addition salts and a process and novel intermediates for their preparation.

It is another object of the invention to provide novel central analgesic compositions and a method of relieving pain in warm-blooded animals.

These and other objects and advantages of the invention will become obvious from the following detailed description.

THE INVENTION

The novel compounds of the invention are selected from the group consisting of all possible racemic, enantiomeric and diastereoisomeric forms of a compound of the formula

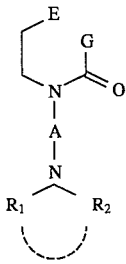

I wherein E and G together form a group selected from the group:

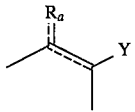

consisting of a)

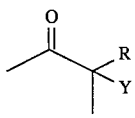

or, if appropriate, its tautomer

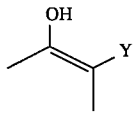

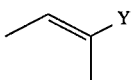

and

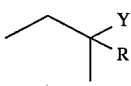

or E is —COOR$_3$ and G is

R is selected from the group consisting of hydrogen alkyl of 1 to 6 carbon atoms, alkenyl or alkynyl of 2 to 6 carbon atoms optionally substituted with aryl radicals of 6 to 14 carbon atoms optionally substituted with at least one member of the group consisting of halogen, —OH, —CF$_3$, alkoxy of 1 to 6 carbon atoms, —NO$_2$, —CN, —NH$_2$, or with the radicals selected from the group consisting of free and esterified or salified carboxy, acyl of 1 to 7 carbon atoms, alkoxy of 1 to 6 carbon atoms, —OH, —NH$_2$, alkylamino, dialkylamino, acyloxy of 1 to 7 carbon atoms, —CN, carbamoyl and halogen, Y is selected from the group consisting of carbocylic aryl of 6 to 14 carbon atoms, heteromonocyclic aryl of 5 to 7 ring members and condensed heterocyclic aryl, all optionally substituted, R$_3$ is hydrogen or alkyl of 1 to 4 carbon atoms, A is an optionally substituted carbocyclic or

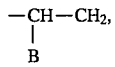

B is selected from the group consisting of hydrogen, optionally substituted aryl of 6 to 14 carbon atoms, optionally substituted aralkyl of 7 to 14 carbon atoms, optionally substituted cycloalkyl of 3 to 7 carbon atoms, optionally substituted alkyl of 1 to 7 carbon atoms and optionally substituted alkenyl and alkynyl of 2 to 7 carbon atoms, R$_1$ and R$_2$ are individually selected from the group consisting of hydrogen, optionally substituted alkyl of 1 to 7 carbon atoms and optionally substituted alkenyl and alkynyl of 2 to 7 carbon atoms or R$_1$ and R$_2$ together with the nitrogen to which they are attached form an optionally substituted, optionally unsaturated heterocycle of 5 to 7 member rings optionally containing another hetero atom selected from the group consisting of —O—, —S— and —N— and their non-toxic, pharmaceutically acceptable salts with acids and bases.

In the compounds of formula I, aryl which can be R, Y and B is a carbocyclic aryl for R and an optionally substituted carbocyclic or heterocyclic for Y and B. Examples of an optionally substituted aryl are phenyl, naphthyl, for example 1-naphthyl; indenyl; a saturated or unsaturated heterocyclic of 5, 6 or 7 links containing at least one heteroatom chosen from sulfur, nitrogen and oxygen. When the heterocyclic contains more than one heteroatom, the heteroatoms of this heterocyclic group can be identical or different. Examples of such aryl are thienyls such as 2-thienyl and 3-thienyl, furyl such as 2-furyl, pyridyl such as 3-pyridyl, pyrimidyl, pyrrolyl, N-substituted pyrrolyl, such as N-methyl pyrrolyl, thiazolyl, isothiazolyl, diazolyl, triazolyl, tetrazolyl, thiadiazolyl, thiatriazolyl, oxazolyl, oxadiazolyl, 3- or 4-isoxazolyl, substituted 3- or 4-isoxazolyl such as 3-aryl-5-methyl isoxazol-4-yl. The aryl may be phenyl or halophenyl and examples of condensed heterocyclics containing at least one heteroatom chosen from sulfur, nitrogen and oxygen are benzothienyl such as 3-benzothienyl, benzofuryl, benzopyrrolyl, benzimidazolyl, benzoxazolyl, thionaphthyl, indolyl or purinyl.

The term aralkyl includes an optionally substituted carbocyclic or heterocyclic aryl in which the lower alkyl contains 1 to 4 carbon atoms such as benzyl, phenethyl, diphenylmethyl, triphenylmethyl, thienylmethyl such as 2-thienylmethyl, furylmethyl such as furfuryl, pyridylmethyl or pyrrolylmethyl, the aryl and aralkyl being able to contain at least one substituent selected from the group consisting of halogens such as chlorine or bromine as in o-chlorophenyl; hydroxy; lower alkyl such as methyl, ethyl, or isopropyl or tertbutyl; alkenyl; alkynyl; trihaloalkyl such as trifluoromethyl; trihaloalkylthio such as for example, trifluoromethylthio; trihaloalkyloxy such as trifluoromethoxy; cyano; nitro; amino; substituted amino such as methylamino or ethylamino, lower dialkyl amino such as dimethylamino; sulfamoyl; lower alkanoyl such as formyl, acetyl; benzoyl; lower alkanoyl amido; lower alkyloxy such as methoxy, ethoxy, or isopropoxy; lower alkylthio such as methylthio or ethylthio; free or esterified carboxy such as methoxycarbonyl or ethoxycarbonyl; carbamoyl; substituted carbamoyl; or aryl such as phenyl.

The term carbocyclic which can be represented by A includes cycloalkyl, cycloalkenyl and cycloalkadienyl or an optionally substituted non-aromatic. Examples of optionally substituted carbocyclics are cyclohexyl, cyclopentyl, cyclobutyl, cyclopropyl, 1,3-cyclohexadienyl, 1,4-cyclohexadienyl, dimethyl-1,3-cyclohexenyl.

Among the values of A as a carbocyclic are preferably the optionally substituted cycloalkyls of the formula

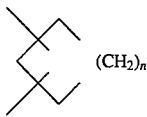

in which n is an integer from 0 to 4, preferably 2 and 3. Cycloalkyl of 3 to 7 carbons for B are preferably cyclopropyl, cyclobutyl, cyclopentyl or cyclohexyl.

The term linear or branched alkyl of 1 to 6 carbons includes methyl, ethyl, propyl or isopropyl, but can also be butyl, isobutyl, sec-butyl, tert-butyl or pentyl. The term linear or branched alkenyl of 2 to 6 carbons includes vinyl, allyl, 1-propenyl, butenyl or pentenyl. The term linear or branched alkynyl of 2 to 6 carbons includes ethynyl, propargyl, butynyl or pentynyl. The term linear or branched alkoxy of 1 to 6 carbons includes preferably methoxy or ethoxy but can also be a linear, secondary or tertiary propoxy, isopropoxy or butoxy.

The term acyl of 1 to 7 carbons preferably includes formyl, acetyl, propionyl or benzoyl and acyloxy of 1 to 7 carbons encompasses acyl of one of the groups named above.

The carbocylics such as cycloalkyl and the alkyl, alkenyl alkynyl or alkyloxy groups can be substituted with at least one substituent selected from the group consisting of halogen, such as chloro or bromo as in 2-bromoethyl; hydroxy; alkyl; alkenyl; alkynyl; aryl such as phenyl or naphthyl; aralkyl such as benzyl or phenethyl; cycloalkyl such as cylcopropyl, cyclopentyl or cyclohexyl; alkoxy such as methoxy, ethoxy propoxy or isopropoxy or methoxymethyl or 1- ethoxyethyl; aryloxy such as phenoxy; aralkyloxy such as benzyloxy; mercapto; alkylthio such as methylthio or ethylthio; arylthio, aralkyl thio; amino such as 2-aminoethyl; substituted amino such as monoalkylamino such as methylamino or ethylamino, dialkylamino such as dimethylamino; nitro; cyano; azido; carboxy; esterified carboxy such as methoxycarbonyl or ethoxycarbonyl; formyl; acyl such as acetyl, propionyl or benzoyl; acyloxy such as acetoxy or propionyloxy; cyano phthalimido; acylamino such as acetamido or benzamido; alkyloxycarbonylamino such as methoxycarbonylamino or ethoxycarbonylamino; or aralkyl oxycarbonylamino such as benzyloxycarbonylamino.

When $R_1$ and $R_2$ combine with the nitrogen atom to which they are attached to form a heterocycle, it is preferably pyrrolidino, piperidino, morpholino or piperazinyl. The second nitrogen atom that can be contained in the heterocycle formed by $R_1$ and $R_2$ can be substituted, for example, by a linear or branched alkyl or alkoxy of 1 to 5 carbon atoms, phenyl or benzyl optionally substituted by the substituents already mentioned above for aryl and aralkyl. There can be cited as examples methylpiperazinyl, ethylpiperazinyl, propylpiperazinyl, phenylpiperazinyl or benzylpiperazinyl.

In the products of formula I, the term halogen preferably is chlorine, but can also be fluorine, bromine or iodine. The term monoalkyl- or dialkylamino preferably is monoalkyl- or dialkylamino in which the alkyl contains 1 to 5 carbon atoms and especially methyl, ethyl or isopropyl. The term acyl of 2 to 6 carbon atoms preferably is acetyl, propionyl, butyryl or benzoyl but also includes valeryl, hexanoyl, acryloyl, crotonoyl or carbamoyl.

The term esterified carboxy preferably includes lower alkoxycarbonyl such as methoxycarbonyl, ethoxycarbonyl or benzyloxycarbonyl and the substituted carbamoyl radical includes lower N-monoalkyl carbamoyl such as N-methylcarbamoyl, N-ethylcarbamoyl; a lower N,N-diethylcarbamoyl; an N-(lower hydroxylalkyl) carbamoyl such as N-(hydroxymethyl) carbamoyl, N-(hydroxyethyl) carbamoyl; and lower carbamoylalkyl such as carbamoylmethyl, carbamoylethyl.

Among the substituents that can be on the aryl, and more particularly the phenyl for R, Y and B cited, for example, are halogen such as chloro and bromo; hydroxy; alkyl such as methyl, ethyl, iso-propyl or tert-butyl; alkenyl; alkynyl; alkoxy, such as methoxy, ethoxy or isopropoxy; alkyl, alkenyl, alkynyl or alkoxy substituted by at least one member selected from the group consisting of hydroxy, linear or branched alkyl and alkoxy such as methyl, ethyl, tert-butyl, methoxy, ethoxy, isopropoxy; substituted amino such as monoalkyl- and dialkylamino like methylamino, ethylamino or dimethylamino.

The non-toxic, pharmaceutically acceptable acid addition salts may be salts formed with inorganic acids such as hydrochloric acid, hydrobromic acid, hydroiodic acid, nitric acid, sulfuric acid and phosphoric acid, organic acids such as propionic acid, acetic acid, formic acid, benzoic acid, maleic acid, fumaric acid, succinic acid tartaric acid, citric acid oxalic acid, glyoxylic acid, aspartic acid, ascorbic acid, alkylmonosulfonic acids such as methanesulfonic acid, ethanesulfonic acid, propanesulfonic acid, alkyldisulfonic acids such as methanedisulfonic acid, alpha, beta-ethanedisulfonic acid, arylmonosulfonic acids such as benzenesulfonic and the aryldisulfonic acids such as paratoluene sulphonic acid.

The salts of bases can be salts of sodium, potassium, lithium, calcium, magnesium or ammonium, salts of organic bases such as methylamine, propylamine, trimethylamine, diethylamine, triethylamine, N,N-dimethylethanolamine, tris-(hydroxymethyl)amino methane, ethanolamine, pyridine, picoline, dicyclohexylamine, morpholine, benzylamine, procaine, lysine, arginine, histidine or N-methylglu-camine.

When A is

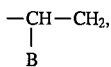

the products of formula I can be presented in one of the two following forms:

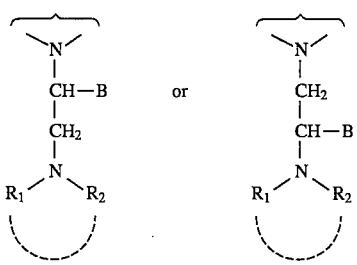

When A is a substituted cycloalkyl, the products in which the substituents are in the trans position are preferred.

Among the preferred compounds of formula I are those of the formula

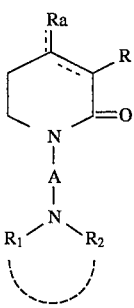

in which A, $R_1$ and $R_2$ and the group

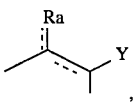

are as defined above and especially those in which the group

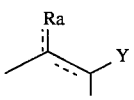

is

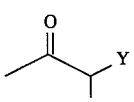

or if appropriate its tautomer

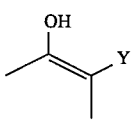

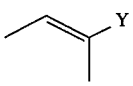

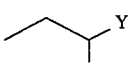

Y being defined as above, as well as those of the formula:

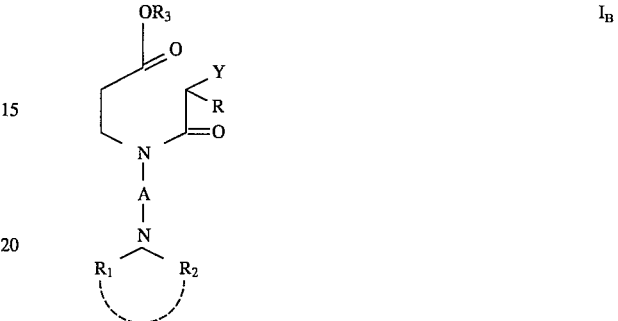

in which $R_1$, $R_2$, $R_3$, A, R and Y are as defined above.

Among the preferred compounds of formula I are those wherein the substituents carried by aryl, aralkyl and heterocyclics or those that can be formed by $R_1$ and $R_2$ with the nitrogen atom to which they are attached are selected from the group consisting of halogen, alkyl, alkenyl, alkynyl or alkoxy of at most 7 carbon atoms and optionally substituted hydroxy, trifluoromethyl, trifluoromethylthio, trifluoromethoxy, cyano, nitro, sulfamoyl, amino, monoalkyl and dialkylamino, formyl, acyl of 2 to 6 carbon atoms, and benzoyl, free carboxy or esterified by alkyl of 1 to 5 carbon atoms and salified, carbamoyl optionally substituted by at least one member selected from the group consisting of alkyl, alkoxy, hydroxyalkyl and carbamoylalkyl, the alkyl and alkoxy having 1 to 4 carbon atoms, phenyl or benzyl optionally substituted by at least one member selected from the group consisting of halogen, hydroxy, cyano, nitro, alkyl, alkenyl, and alkynyl and alkoxy of at most 5 carbon atoms, products of formula I being in all possible racemic, enantiomer and diastereoisomer isomer forms, as well as the addition salts with mineral and organic acids or with the bases of products of formula I.

Also preferred are the compounds of formula I as defined above wherein the substituents carried on alkyl, alkenyl, alkynyl, cycloalkyl, carbocyclic and alkyloxy are selected from the group consisting of halogen, alkyl, alkenyl, alkynyl or alkoxy of at most 5 carbon atoms, formyl, acyl of 2 to 6 carbon atoms and benzoyl, free carboxy or esterified with alkyl of 1 to 5 carbon atoms.

Among the preferred compounds of formula I are those wherein R is alkyl, alkenyl and alkynyl optionally substituted with optionally substituted phenyl, those wherein Y is phenyl, naphthyl, thionaphthyl, benzofuryl, benzopyrrolyl or indenyl optionally substituted by at least one member selected from the group consisting of halogen, alkyl, alkenyl, alkynyl or alkoxy of at most 7 carbon atoms optionally substituted by at least one member selected from the group consisting of hydroxy and alkyl and alkyloxy of 1 to 5 carbon atoms, acyl of 2 to 6 carbon atoms, trifluoromethyl, cyano, nitro, amino, monoalkyl- and dialkylamino of 1 to 5 carbon atoms, and phenyl optionally substituted by at least one member of the group consisting of halogen, hydroxy, cyano, nitro, alkyl, alkenyl, alkynyl and alkoxy of at most 5 carbon atoms; and those wherein A is either cycloalkyl of the formula

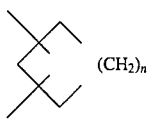

where n is an integer of 0 to 4 optionally substituted by alkyl or alkoxy radical of 1 to 5 carbon atoms,

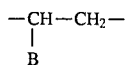

in which B is phenyl optionally substituted by at least one member selected from the group consisting of halogen, hydroxy, cyano, nitro, alkyl, alkenyl, alkynyl and alkoxy of at most 5 carbon atoms, those wherein A is non-substituted cyclohexyl or cyclopentyl and those wherein the heterocycle formed by $R_1$ and $R_2$ together with the nitrogen atom to which they are linked, is optionally substituted on the second nitrogen atom by alkyl or alkoxy of 1 to 5 carbon atoms such as methyl, ethyl, isopropyl, methoxy or ethoxy.

Among the specific preferred products of formula I are (1S)-3-(3,4-dichlorophenyl)-1-[1-phenyl-2-(1-pyrrolidinyl)-ethyl]-2-piperidinone (isomer B), (1S)-3-(3,4-dichlorophenyl)-1-(1-phenyl-2-(1-pyrrolidinyl)-ethyl)-2-piperidinone (isomer A), [trans, (±)]-3-(3,4-dichlorophenyl)-1-(2-(1-pyrrolidinyl)-cyclohexyl)-2-piperidinone (isomer A), (1S)-3-(3,4-dichlorophenyl)-1-(2-methyl-1-((1-pyrrolidinyl)-methyl)-propyl)-2-piperidinone (isomer A), (1S)-3-(benzo-(b)-thien-4-yl)-1-(1-phenyl-2-(1-pyrrolidinyl)-ethyl)-2-piperidinone (isomer A), (1S)-3-(3,4-dichlorophenyl)-3-methyl-1-(1-phenyl-2-(1-pyrrolidinyl)-ethyl)- 2-piperidinone (isomer A), (1S)-3-(3,4-dichlorophenyl)-3-ethyl-1-(1-phenyl-2-(1-pyrrolidinyl)-ethyl)- 2-piperidinone (isomer A), (1S)-3-(3,4-dichlorophenyl)-1-(1-phenyl-2-(1-pyrrolidinyl)-ethyl-3-(2-propenyl)- 2-piperidinone (isomer A), ethyl (S)-3-(((3,4-dichlorophenyl)-acetyl)-(1-phenyl-2-(1-pyrrolidinyl)-ethyl)-amino) propanoate, ethyl (S)-3-(((benzo-(b)-thien-4-yl)-acetyl)-(1-phenyl-2-(1-pyrrolidinyl)-ethyl)-amino) propanoate, ethyl (S)-3-(((4-trifluoromethyl)-acetyl)-(1-phenyl-2-(1-pyrrolidinyl)-ethyl)-amino) propanoate and if appropriate, their salts.

The novel process of the invention for the preparation of the products of formula I comprises reacting a diamine of the formula:

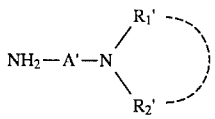 II in which A' and
have the above meanings for
A and

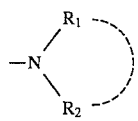

or those in which the reactive functions that can be carried by

A and

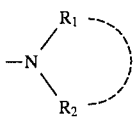

are protected with an acrylic ester of the formula $$CH_2=CHCOOR_3 \quad \quad III$$

in which $R_3$ is alkyl of 1 to 6 carbon atoms to obtain condensed product of the formula

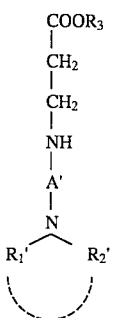 IV in which A',
and $R_3$ have the above meanings, reacting the latter with a compound of the formula

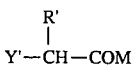 V in which R' is hydrogen or the values of R indicated above or those in which the reactive functions are protected, M is hydroxyl or halogen and Y' has the values of Y indicated above, or those in which the reactive functions are protected to obtain a product of the formula:

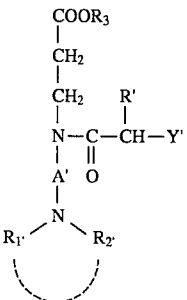 VI in which A',

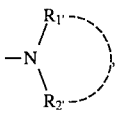

R', $R_3$ and Y' have the above meanings corresponding to the case where R' is hydrogen or the values of R and A', $NR'_1 R'_2$ and Y' are respectively the values of A, $NR_1R_2$ and Y, to form a product of formula $I_B$ as defined above, product of formula VI in which if appropriate, the protective groups are eliminated to obtain the same product of formula $I_B$ or which is optionally subjected to a cyclization reaction to obtain a product of the formula:

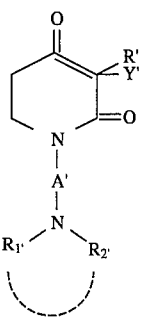

VII

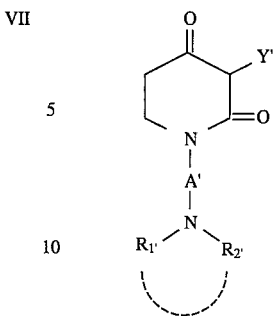

IX in which A',

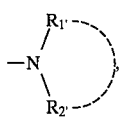

in which A',

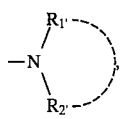

R' and Y' have the above meanings, corresponding to the case where R' is hydrogen or the values of R and A', NR'$_1$R'$_2$ and Y' are respectively the values of A, NR$_1$R$_2$ and Y, to form a product of formula I$_A$ as define above called I$_{A1}$, product of formula VII in which if appropriate, the protective groups are eliminated to obtain the same product of formula I$_{A1}$, then, if appropriate: either, when R' or R is hydrogen, the said product of formula VII or I$_{A1}$ is subjected: either to a reduction reaction of the oxo function in gamma position of the nitrogen atom to obtain the product of the formula:

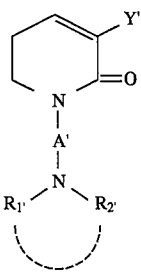

VIII in which A',

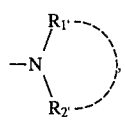

and Y' have the above meaning, corresponding to the case where Y', A' and NR'$_1$R'$_2$ have respectively the values of Y, A and NR$_1$R$_2$, to a product of formula I$_A$ as defined above, called I$_{A2}$, the product of formula VIII in which, if appropriate, the protective groups are eliminated to obtain the same product of formula I$_{A2}$, or to a reduction reaction by catalytic hydrogenation of the same oxo function to obtain the product of the formula:

and Y' have the above meanings, corresponding to the case where Y', A' and NR'$_1$R'$_2$ have respectively the values of Y, A and NR$_1$R$_2$, to a product of formula I$_A$ as defined above, called I$_{A3}$, the product of formula IX in which, if appropriate, the protective groups are eliminated to obtain the same product of formula I$_{A3}$, product of formula IX or I$_{A3}$ which is optionally treated with a strong base to form the corresponding anion, which is subjected to the action of a reagent capable of grafting a R' having the above values with the exception of hydrogen to obtain a product of the formula:

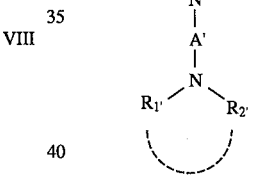

X in which R', Y', A' and

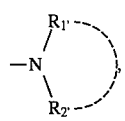

have the above values, corresponding to the case R', Y', A' and NR'$_1$R'$_2$ have respectively the values of R with the exception of hydrogen, Y, A and NR$_1$R$_2$, to a product of formula I$_A$ as defined above, called I$_{A4}$, product of formula X in which, if appropriate, the protective groups are eliminated to obtain the same product of formula I$_{A4}$; or when R' or R is not hydrogen, the said product of formula VII or I$_{A1}$ is subjected to a reduction agent of the oxo function to obtain the product of formula X as defined previously which either corresponds to a product of formula I$_{A4}$ or is converted into this product of formula I$_{A4}$, and, if desired, the products of formula I are treated with a mineral or organic acid to obtain the corresponding salt, said products of formula I being in all possible racemic, enantiomer and diastereoisomer isomer forms.

Preferably, the condensation reaction of the diamine of formula II with an acrylic ester of formula III in which $R_3$ is alkyl such as ethyl or methyl acrylate but which can also be butyl acrylate can be carried out in a solvent such as an alcohol like ethanol, methanol or butanol. First the solution can be cooled to a temperature of about 10° C., then left to return to ambient temperature with stirring so that the addition reaction forming the product of formula IV takes place.

In the reaction to obtain the amide of formula VI, the acylation of the secondary amine of formula IV can be carried out by known methods for example, by the acid of formula V in which M is hydroxy in the presence of N,N'-carbonyldiimidazole or cyclohexylcarbodiimide or by the acid halide of formula V in which M is halogen such as chlorine. The reaction according to commonly used processes takes place in an organic solvent such as tetrahydrofuran or a chlorinated solvent such as methylene chloride with stirring at ambient temperature.

The cyclization reaction of the product of formula VI into the corresponding product of formula VII can be carried out in a basic medium such as sodium or potassium hydride or an alcoholate such as potassium or sodium terbutylate in an organic solvent such as tetrahydrofuran, toluene or ether. The reaction medium can first be slowly cooled to a temperature of 12° C. to 15° C., then taken to ambient temperature or heated at reflux.

The reduction of the product of formula VII or $I_{A1}$ into the product of formula VIII or $I_{A2}$ can be effected by the conversion of the oxo function of the formula VII into hydrazone by a reagent such as an arylsulfonyl hydrazine such as p-toluenesulfonyl hydrazine in an organic solvent such as acetic acid or an alcohol such as methanol or ethanol at ambient temperature. The reduced product of formula VIII can be obtained by decomposition of the intermediate hydrazone, the decomposition being carried out by sodium or potassium alcoholate such as sodium ethylate or sodium or potassium methylate or butylate. The reaction is carried out in a hydroxylated solvent such as hot ethylene glycol at a temperature of approximately 120° C. to 160° C.

The reduction reaction of the product of formula VIII or $I_{A2}$ into a product of formula IX or $I_{A3}$ can be carried out by catalytic hydrogenation of the ethylene function in the presence of a hydracid such as hydrochloric acid or hydrobromic acid. The reaction is carried out in an alcohol such as ethanol in acetic acid or in an acid ester such as ethyl acetate, on platinum oxide at ambient temperature. The reduction reaction of the product of formula VIII into the product of formula IX can also be carried out by the action of a mixed hydride, for example, sodium borohydride in an organic solvent, for example, a lower alcohol, preferably ethanol. The strong base used in preferably an alkaline alcoholate i.e. potassium terbutylate.

The agent capable of grafting R' onto the product of formula IX or $I_{A3}$ can be an alkyl sulfonate but is preferably a halide. The alkyl sulfonate can be a mesylate but is preferably a tosylate. The halide can be a chloride but is preferably a bromide or an iodide.

The reduction of the oxo function of the product of formula VII in which R or R' is not hydrogen is carried out under identical conditions to those indicated above for the obtaining of the product of formula VIII.

In the products of formula V, VII, VIII, IX and X, the various reactive functions that can, if necessary, be protected by appropriate protective groups are, for example, hydroxyl, acyl, free carboxy and amino and monoalkylamino. The following non-exhaustive list of examples of protection of reactive functions can be cited: The hydroxy can be protected by trimethylsilyl, dihydropyran, benzyl, methoxy or methoxymethyl and the aminos can be protected by trityl, benzyl, terbutoxycarbonyl, phthalimide or other groups known in the chemistry of peptides.

The acyl such as formyl can be protected in the form of cyclic or non-cyclic ketals such as dimethyl- or diethylketal or ethylene dioxyketal and the carboxy groups can be protected in the form of esters formed with easily cleavable esters such as benzyl or terbutyl esters or esters known in the chemistry of the peptides.

The elimination of these protective groups is effected under the usual known conditions, notably acid hydrolysis carried out with an acid such as hydrochloric and benzene sulfonic acid or paratoluene sulfonic acid, formic acid or trifluroacetic acid. The phthalimido group is eliminated by hydrazine. A list of the different protective groups which can be used will be found, for example, in the Patent BF 2,499,995.

Also a subject of the invention is a preparation process for products of formula I as defined above, characterized in that the starting process of the products of formula IV as defined above is implemented and the process as indicated above is carried out. The optically active forms of the products of formula I can be prepared by resolution of the racemics according to the usual methods.

The novel central analgesic compositions of the invention are comprised of a central analgesically effective amount of at least one compound of formula I and its non-toxic, pharmaceutically acceptable salts with acids or bases and an inert pharmaceutical carrier. The compositions may be in the form of tablets dragees, capsules, granules, suppositories, injectable solutions or suspensions, ointments, creams, gels and aerosol preparations.

Examples of the suitable excipients are talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying agents, and preservatives.

The compositions show a strong affinity for opiate receptors and notably for the kappa receptors and are endowed with central analgesic properties. They are also endowed with diuretic properties, anti-arythmic properties, cerebral anti-ischemic properties and hypotensive properties.

The compositions are useful for the relief of pain of whatever origin, for example, pain of muscular, articular or nervous nature. They are also useful in the treatment of toothaches, migraines, shingles, in the treatment of intense pains, especially those resistant to peripheral analgesics, for example in the course of the neoplasia process, in the treatment of pancreatitis, nephretic or biliary colics, in the treatment of post-operative and post-traumatic pain. They can also be used in the treatment of cerebral deficiencies of an ischemic origin, and in disorders of memory and concentration. They are also useful in the treatment of hyponatremial situations and inappropriate water retention, such as those observed in edematous syndromes, cardiac deficiency, certain obesities, cyrrhosis, in the treatment of severe and refractory edemas, such as cerebral edemas and those of congestive cardiac deficiencies as well as in the long-term treatment of arterial hypertension.

The novel method of the invention for relieving pain in warm-blooded animals, including humans, comprises administering to warm-blooded animals an analgesically effective amount of at least one compound of formula I and its non-toxic, pharmaceutically acceptable salts with acids or bases. The compounds may be administered bucally, rectally, parenterally or topically to the skin or mucous membranes. The usual daily dose is 0.0666 to 5.333 mg/kg depending on the specific condition treated, the specific compound and the method of administration.

The starting products of the formula:

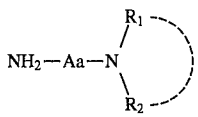  IIa in which Aa is cyclohexyl and $R_1$ and $R_2$ have the above meaning are known, for example, from

CA 072–078 895

CA 52–P 5460

U.S. Pat. No. 728,779

Other known starting products are the products of the formula:

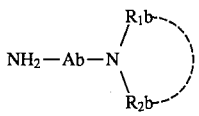  IIb in which Ab is

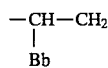

and Bb is phenyl and

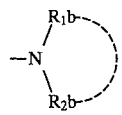

is pyrrolidinyl which are described in

CA 074–141 142

CA 102–149 185

CA 084–121 724

Certain starting products are new and non-exhaustive examples of the preparation of these starting products can be indicated, as follows: The products of formula II as defined above in which A' is

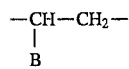

and B has the above meaning can be prepared by reacting a compound of the formula:

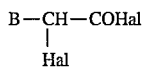  F in which B has the above meaning and Hal is hydrogen, with ammonium hydroxide to obtain the corresponding amide of the formula:

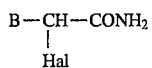  G in which Hal and B have the above meanings, reacting the latter with an amine of the formula:

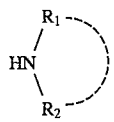  H in which $R_1$ and $R_2$ have the above meanings to obtain the corresponding amide of the formula:

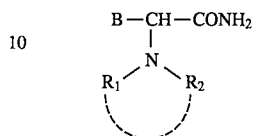  K in which B, $R_1$ and $R_2$ have the above meanings, and reducing the amide function by standard processes to obtain the corresponding product of formula II.

The products of formula II in which A is carbocyclic can be prepared from commercially available benzylamine which is reacted with cyclohexyl oxide in an aqueous medium to obtain a compound of the formula:

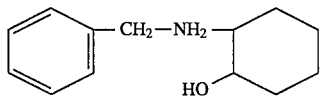  L reacting the latter with chlorosulfonic acid in the presence of methylene chloride to obtain the sulfated derivative of the formula:

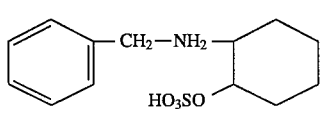  M which is reacted with sodium hydroxide in an aqueous medium to obtain the corresponding aziridine of the formula:

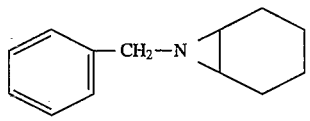  N which is reacted in the presence of ammonium chloride with the amine of the formula:

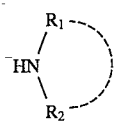  H in which $R_1$ and $R_2$ have the above meanings, to obtain the compound of the formula:

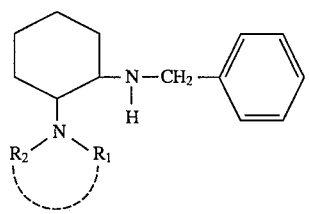  O which is debenzylated by catalytic hydrogenation to obtain the corresponding product of formula II.

The other starting products of formula II can be prepared by comparable methods known to the ordinarily skilled artisan. The invention also relates to, as new industrial products, the compounds of formulae IV, VI, VII, VIII, IX and X.

In the following examples, there are described several preferred embodiments to illustrate the invention. However, it is to be understood that the invention is not intended to be limited to the specific embodiments.

EXAMPLE 1

Ethyl [trans, (±)]-3-[[2-(1-pyrrolidinyl)cyclohexyl]-[(3,4-dichlorophenyl)-ecetyl]-amino]propanoate Stage A: Ethyl [trans, (±)]-3-[[2-(1-pyrrolidinyl)cyclohexyl]-amino]propanoate.

5.4 cm³ of ethyl acrylate in solution in 50 cm³ of ethanol are added over 30 minutes to solution of 8.4 g of 2-(1-pyrrolidinyl) cyclohexane amine in 50 cm³ of ethanol, cooled to ±10° C. Agitation takes place for 6 hours at ambient temperature. After evaporating to dryness, 12.7 g of product is collected and is used as it is for the following stage.

IR Spectrum (CHCl₃)

| | |
|---|---|
| —C— ‖ O | 1726 cm⁻¹ |
| —NH | 3260 cm⁻¹ |

RMN (CDCl₃)

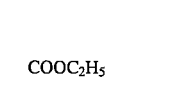

| | |
|---|---|
| 1.25 (t) 4.13 (q) | COOC₂H₅ |
| 2.52 | CH—N  axial |
| 0.95 to 3.0 | the other protons |

Stage B: Ethyl [trans, (±)]-3-[[2-(1-pyrrolidinyl)cyclohexyl]-[(3,4-dichlorophenyl)-acetyl]-amino]propanoate.

A mixture of 10.65 g of 3,4-dichlorophenyl acetic acid, 8.40 g of carbonyldiimidazole and 70 cm³ of anhydrous tetrahydrofuran are agitated for 1 hour at ambient temperature. A solution of 12.65 g of the amine obtained in Stage A in 70 cm³ of anhydrous tetrahydrofuran is added over 10 minutes. Agitation takes place for 5 hours at ambient temperature. Extraction takes place with ethyl acetate, followed by washing with 120 cm³ of a saturated solution of sodium bicarbonate then twice with 70 cm³ of water, drying and concentrating to dryness under reduced pressure. The residue 22 g, is chromatographed on silica (eluant: ethyl acetate—triethylamine (97–3)). 17.6 g of expected product is obtained and is used as it is for the following stage:

IR Spectrum

| | |
|---|---|
| 1725 cm⁻¹ | —C— ester region ‖ O |
| 1730 cm⁻¹ | tertiary amide |

EXAMPLE 2

[Trans, (±)]-3-(3,4-dichlorophenyl)-1-[2-(1-pyrrolidinyl)-cyclohexyl]-2,4-piperidinedione and its hydrochloride.

a) Preparation of the Base.

A solution of 15.14 g of the product obtained in Example 1, in 50 cm³ of anhydrous tetrahydrofuran is added over 15 minutes at 0°/+5° C. to an agitated suspension of 0° C. at 2.4 g of sodium hydride (at 50% in oil) and 100 cm³ of anhydrous tetrahydrofuran. Agitation takes place for 1 hour 45 minutes whilst leaving the medium to return to ambient temperature, then for an extra 2 hours ambient temperature (a release of hydrogen is observed), then concentration to dryness under reduced pressure takes place and the residue is taken up in 150 cm³ of water and ice. After extracting the solution twice with 100 cm³ of sulphuric ether, the aqueous phase is acidified with 5 cm³ of acetic acid. Then 2.5 g of potassium carbonate is added, the whole is agitated at ambient temperature until crystals are obtained which are separated, washed with 3 times 20 cm³ of water, then with 3 times 20 cm³ of ether, the product is dried under reduced pressure at 50° C. 11.75 g of expected product is obtained in the form of a base. M.p.=133° C.

IR Spectrum (Nujol)
Absorption OH/NH

| | |
|---|---|
| —C— ‖ O | 1734 cm⁻¹ (f) 1653 cm⁻¹ |
| absorption | approx. 1603 cm⁻¹ (F complex) |
| Aromatic | 1545 cm⁻¹ 1508 cm⁻¹ | b) Preparation of the Hydrochloride.

1.756 g of the base obtained above is dissolved hot in 10 cm³ of ethanol 95, a light insoluble part is filtered off, rinsed 3 times with 1 cm³ of boiling ethanol 95 and 1 cm³ of a solution of 5.75N hydrochloric ethanol. After cooling to 20° C. and agitating for 1 hour, separation takes place, followed by washing twice with 1 cm³ of ethanol 95, twice with 1 cm³ of ethanol 100 and 3 times with 5 cm³ of ether. After drying under reduced pressure at 70° C., 1.484 g of sought product is obtained. M.p.>>260° C.

| | Analysis for C₂₁H₂₆Cl₂N₂O₂, HCl | | | |
|---|---|---|---|---|
| | C % | H % | N % | Cl % |
| % calculated | 56.58 | 6.10 | 6.28 | 23.85 |
| % found | 56.5 | 6.2 | 6.2 | 23.6 |

NMR DMSO (250 MHz)

| | |
|---|---|
| 4.38 (m) | CH—N—C— axial ‖ O |
| 3.66 (dt, j = 3.5 11 and 11) | CH—N axial |

-continued

| | |
|---|---|
| 2.64 (m) 1H<br>2.84 (m) 1H<br>3.2 to 3.6 | the other H's in alpha position of N |
| 7.27 (dd) 1H<br>7.47 2H | aromatics |
| 1.2 to 2.2 | the other protons. |

EXAMPLE 3

[Trans, (±)]-3-(3,4-dichlorophenyl)-5,6-dihydro-1-[2-(1-pyrrolidinyl)-cyclohexyl]-2-(1H)-pyridinone and its fumarate.

Stage A: [Trans, (±)]-2-[3-(3,4-dichlorophenyl)-2-oxo-1-[2 -(1-pyrrolidinyl)-cyclohexyl]-1,2,5,6-tetrahydro-4-pyridyl]hydrazide of 4-methyl benzene sulphonic acid.

A mixture of 5 g of the base obtained in Example 2, 2.95 g of paratoluene sulphonyl hydrazide and 25 cm³ of acetic acid are agitated for 4 hours at ambient temperature. 150 cm³ of water saturated with sodium chloride is added to the reaction medium, then 50cm³ of sulphuric ether is added, and agitation takes place for 2 hours at ambient temperature. After separating, the whole is washed with 20 cm³ of water saturated with sodium chloride and 5 cm³ of sulphuric ether, then with a solution of potassium carbonate at 15% with water and with ether. After drying under reduced pressure at 20° C., 6.25 g of expected product is obtained, M.p.=approx. 200° C., which is used as it is for the following stage.

IR Spectrum (CHCl₃)

| | |
|---|---|
| —SO₂— | 1336–1165 cm⁻¹ |
| C=O | 1627 cm⁻¹ |
| C=C region | 1601, 1545, 1490, 1474 cm⁻¹ |
| C=N<br>=C—NH | approx. 3360 cm⁻¹ complex |

Stage B: [Trans, (±)]- 3-(3,4-dichlorophenyl)-5,6 -dihydro-1-[2-(1-pyrrolidinyl)-cyclohexyl]-2-(1H)-pyridinone and its fumarate.
a) Preparation of the Base.

0.65 g of sodium is introduced over 30 minutes at 20° to 35° C. into 28 cm³ of ethanol 100, then heated to 60° C. and 5.64 g of the product obtained in Stage A and 22 cm³ of ethylene glycol are added. The ethanol is distilled off at standard pressure then heating takes place for 30 minutes to 160° C. in the reaction medium until no more gas is released. After cooling to 20° C. and extracting with methylene chloride, the extracts are dried, filtered and concentrated to dryness under reduced pressure, 3.78 g of product is collected in the form of the base. 1.319 g of the base obtained is chromatographed on silica (eluant: ethyl acetate with 0.5% triethylamine).
b) Preparation of the Fumarate:

0.63 g of the product obtained after chromatography is dissolved in 5 cm³ of ethanol, 248 mg of the fumaric acid is added and the whole is taken to reflux. After separating at 20° C., washing 3 times with 0.5 cm³ of ethanol then 3 times with 5 cm³ of ether and drying, 0.681 g of desired product is obtained. M.p.=202° C.

| Analysis for C₂₁H₂₆Cl₂N₂O, 1,5 (C₄H₄O₄) | | | | |
|---|---|---|---|---|
| | C % | H % | N % | Cl % |
| % calculated | 57.14 | 5.68 | 4.94 | 12.49 |
| % found | 57.1 | 5.9 | 4.9 | 12.5 |

NMR CDCl₃ (250 MHz)

| | |
|---|---|
| 6.59 (t, j approx. 4,5) | 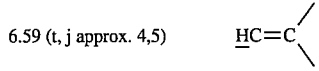 |
| 7.50 (d)<br>7.32 (d)<br>7.23 (dd) | 3H aromatics |
| 4.47 (dt) | 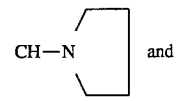 CH—N—C axial (isomer trans)<br>$\|$<br>O |
| 3.30 (m) | CH₂—N—C<br>$\|$<br>O |
| 2.25 to 2.80 7H, | CH₂ in alpha position of N pyrrolidine,<br><br>CH—N⟩ and |
| 0.8 to 1.9 | CH₂—C=C=C—C₆H₅<br>the other protons. |

EXAMPLE 4

[Trans, (±)]-3-(3,4-dichlorophenyl)-1-[2 -(1-pyrrolidinyl)-cyclohexyl]-2-piperidinone (B isomer) and its hydrochloride.

EXAMPLE 5

[Trans, (±)]-3-(3,4-dichlorophenyl)-1-[2 -(1-pyrrolidinyl)-cyclohexyl]-2-piperidinone (isomer A) and its fumarate.

0.56 g of 80% platinum oxide is added to a solution of 5.61 g of the product obtained in Stage B of Example 3 in 112 cm³ of ethanol 100 and 11.2 cm³ of 37% hydrochloric acid and agitation takes place under a hydrogen atmosphere (under a pressure of 1835 mbars) for 4 hours 30 minutes (until a total of 473 cm³ of hydrogen is absorbed). The catalyst is filtered off and the filtrate is evaporated to dryness under reduced pressure. The residue is taken up in 10 cm³ of water and 50 cm³ of ethyl acetate, alkalinization is carried out using an excess sodium carbonate followed by decantation, the aqueous phase is reextracted with 30 cm³ of ethyl acetate, the organic extracts are washed with salt water, then dried, filtered and brought to dryness under reduced pressure. The residue (5.45 g) is chromatographed on silica (eluant: ethyl acetate with 0.5% triethylamine (isolation of isomer A) then ethyl acetate with 1% then with 2% triethylamine for isomer B). In this way 2.452 g of isomer A M.p.=109° C. 2.359 g of isomer B are collected.

Product of Example 4

Hydrochloride of Isomer B.

2.359 g of the obtained isomer B is dissolved in 2 cm³ of ethanol, 4 cm³ of a 1.68N solution of hydrochloric ethanol (pH 1) is added. After separating, washing with ethanol at +5°/+10° C., then with sulphuric ether, and drying, 1.813 g of sought product is obtained. M.p.>260° C. 1.778 g of the hydrochloride obtained above is recrystallised from 25 cm³ of isopropanol and 1.498 g of expected product is obtained. M.p.>260° C.

| Analysis for $C_{21}H_{28}Cl_2N_2O$, HCl | | | | |
|---|---|---|---|---|
| | C % | H % | N % | Cl % |
| % calculated | 58.4 | 6.77 | 6.48 | 24.63 |
| % found | 58.6 | 6.7 | 6.6 | 24.5 |

NMR CDCl₃ (250 MHz)

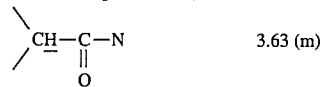  3.63 (m)

7.27 (d)
7.35 (d)  the aromatics
7.05 (d)

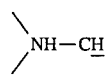  approx. 4.45

2.4 to 2.9  the CH₂N's and the C$\underline{H}$N's 1.0 to 2.2  the other protons.

Product of Example 5

(Isomer A). Fumarate of Isomer A.

2.452 g of isomer A is dissolved hot in 10 cm³ of ethanol, 865 mg of fumaric acid is added. Heating takes place under reflux then the whole is cooled to 20° C. and separated then washed with ethanol then with ether. 2.638 g of sought product is obtained. M.p.=153° C.

| Analysis for $C_{21}H_{28}Cl_2N_2O$, $C_4H_4O_4$ | | | | |
|---|---|---|---|---|
| | C % | H % | N % | Cl % |
| % calculated | 58.71 | 6.31 | 5.48 | 13.86 |
| % found | 58.6 | 6.4 | 5.6 | 14.0 |

NMR CDCl₃ (250 MHz)

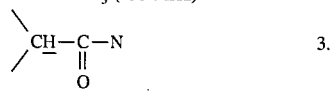  3.63 (t, j = 7)

7.28 (d), 7.34 (d), 7.09 (dd)  the aromatics

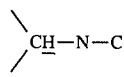  4.61 (dt j = 3, 11, 11)

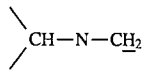  3.2 to 3.4

2.45 to 2.8  C$\underline{H}_2$N and C$\underline{H}$—N 1.07 to 2.2  the other protons.

EXAMPLE 6

Ethyl [Trans, (±)]-3-[[(3,4-dimethoxy phenyl)acetyl]-[2-(1-pyrrolidinyl)-cyclohexyl]-amino]propanoate.

The operation is carried out as in Stage B of Example 1 starting with 16.67 g of product obtained in Stage A of Example 1 and using 14.12 g of 3,4-dimethoxy phenylacetic acid and 11.67 g of carbonyldiimidazol. After chromatography (eluant: ethyl acetate with 1% of triethylamine) 23.69 g of sought product is obtained and is used as it is for the following stage.

IR Spectrum (CHCl₃)
C=O ester       1724 cm⁻¹
C=O amide       1625 cm⁻¹
Aromatics       1592 cm⁻¹
                1514 cm⁻¹   } of the type 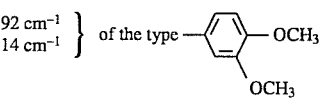

EXAMPLE 7

[Trans, (±)]-3-(3,4-dimethoxy-phenyl)-1-[2-(1-pyrrolidinyl)-cyclohexyl]-2,4-piperidinedione.

The operation is carried out as in Example 2 starting with 5.2 g of the product obtained in Example 6. The product is isolated by taking up the dry extract obtained after evaporation under reduced pressure with water saturated with sodium chloride, followed by separating, washing with hexane and drying under reduced pressure.

3.638 g of expected product is obtained M.p. #260° C. A paste is made of the product with tetrahydrofuran then it is dissolved in a methylene chloride-methanol mixture (7 -3), followed by filtering on clarcel and evaporating to dryness under reduced pressure.

2.935 g of expected product is obtained. M.p. approx. 260° C.

IR Spectrum (Nujol)
OH/NH absorption region 1640 cm⁻¹           weak —C— absorption
                         ‖
                         O 1583 cm⁻¹
1534 cm⁻¹ (ep)   }   aromatic region
1516 cm⁻¹ (max)

EXAMPLE 8

[Trans-(±)]-5,6-dihydro-3-(3,4-dimethoxy-phenyl)-1-[2-(1-pyrrolidinyl)-cyclohexyl]-2-(1H)-pyridinone.

Stage A: [Trans, (±)]-5,6-dihydro-3-(3,4-dimethoxy-phenyl)-4-[2-[(4-methyl-phenyl)-sulphonyl]-hydrazinyl]-1-[2-(1-pyrrolidinyl)-cyclohexyl]-2-(1H)-pyridinone.

The operation is carried out as in Stage A of Example 3 starting with 11.61 g of the product obtained as in Example 7 with 7.02 g of paratoluenesulphonhydrazide, 16.27 g of expected product is obtained, M.p.=195°–200° C., used as it is for the following stage.

After recristallisation of 205 mg of crude product from ethanol, 92 mg of product is obtained. M.p.=238°–240° C.

IR Spectrum ($CHCl_3$)

| =C—NH— | 3340 $cm^{-1}$ (complex) |
|---|---|
| —C— $\parallel$ O | 1628 $cm^{-1}$ |
| Conjugated syst. region +aromatic type (benzene ring with Ome, Ome) | 1601 $cm^{-1}$ 1516 $cm^{-1}$ 1495 $cm^{-1}$ |
| —$SO_2$ | { 1337 $cm^{-1}$ 1165 $cm^{-1}$ |

Stage B: [Trans-(±)]-5,6-dihydro-3-(3,4-dimethoxy-phenyl)-1-[2-(2-pyrrolidinyl)-cyclohexyl]-2-(1H)-pyridinone.

The operation takes place as in Stage B of Example 3 starting with 16.42 g of product obtained in Stage A above, using 1.99 g of sodium and 60 $cm^3$ of ethylene glycol, 12.83 g of sought product is obtained and used as it is in the following example.

EXAMPLE 9

[(1alpha, 2beta) (±)]-3-(3,4-dimethoxy-phenyl)-1-[2-(1-pyrrolidinyl)-cyclohexyl]-2-piperidinone (isomer A and isomer B) and oxalate of isomer B.

The operation takes place as in Example 4 starting with 12.36 g of the product obtained in Example 8, and after chromatography (eluant: first, methylene chloride-methanol (95–5) then (90–10)), 7.84 g of isomer A and 2.8 g of isomer B are obtained. 2.8 g of isomer B are made into a paste with 8 $cm^3$ of sulphuric ether. 0.538 g of product is obtained. M.p.=188°–191° C. The filtrate is chromatographed again and 1.85 g of residue is thus collected which is united with the 0.538 g above to prepare the fumarate in the ethanol which is then crystallized from isopropanol. 1.419 g of fumarate obtained above is returned to the base, by displacement with sodium bicarbonate and sodium carbonate. The dry extract 1.050 g, is dissolved in tetrahydrofuran at 50° C. and 423 mg of dihydrated oxalic acid is added and heated under reflux. After separating at 20° C., washing with tetrahydrofuran then with ethyl ether 987 mg of product is obtained which is recrystallized from tetrahydrofuran with 5% water, after azeotropic elimination of the water, separation takes place and 964 mg of the expected product is obtained. M.p.=192°–196° C.

| Analysis for $C_{23}H_{34}N_2O_3$, $C_2H_2O_4$ | | | |
|---|---|---|---|
| | C % | H % | N % |
| % calculated | 63.01 | 7.61 | 5.88 |
| % found | 62.7 | 7.7 | 5.8 |

EXAMPLE 10

[(1alpha, 2beta) (±)]-3-(3,4-dimethoxy phenyl)-1-[2-(1-pyrrolidinyl)-cyclohexyl]-2-piperidinone (isomer A) and its hydrochloride.

A paste is made with 3.556 g of isomer A obtained in Example 9 in 10 $cm^3$ of sulphuric ether under reflux. 3.31 g of expected product is obtained in the form of a base. M.p.=111°–113° C.

Obtaining the Hydrochloride:

1.6g of the above product is dissolved in 4 $cm^3$ of ethanol 100, 0.4 $cm^3$ of a 6.6N solution of hydrochloric ethanol is added. After separating, washing with ethanol and with ether, 1.326 g of sought product is obtained. M.p.=193° C.

| Analysis for $C_{23}H_{34}N_2O_3$, HCl | | | | |
|---|---|---|---|---|
| | C % | H % | N % | Cl % |
| % calculated | 65.31 | 8.34 | 6.62 | 8.38 |
| % found | 65.3 | 8.4 | 6.4 | 8.5 |

EXAMPLE 11

Ethyl (S)-3-[[(3,4-dichlorophenyl)-acetyl]-[1-phenyl-2-(1-pyrrolidinyl)-ethyl]-amino]-propanoate.

Stage A: Ethyl (S)-3-[[1-phenyl-2-(1-pyrrolidinyl)-ethyl]-amino]propanoate and its dihydrochloride.

The operation takes place as in Stage A of Example 1 starting with 16.19 g of (S)-alpha-phenyl-1-pyrrolidinethanamine and 11 $cm^3$ of ethyl acrylate. Agitation takes place for 40 hours at 20°/22° C. After evaporating to dryness, 22.08 g of crude product is obtained in the form of the base.

Obtaining the Hydrochloride:

22.08 g of the crude product is dissolved in 200 $cm^3$ of ethanol 100 and 25 $cm^3$ of a 6.6N solution of hydrochloric ethanol is added. After separating, washing with ethanol then with ether and drying at 60° C. under reduced pressure, 22.22 g of expected product is obtained. M.p.=245°–250° C. $[alpha]_D$ −19.5°±1(c=1% $H_2O$).

Stage B: Ethyl (S)-3-[[(3,4-dichlorophenyl)-acetyl]-[1-phenyl-2-(1-pyrrolidinyl)-ethyl]-amino]propanoate.

The operation takes place as in Stage B of Example 1 starting with 22.22 g of the hydrochloride obtained in Stage A above, with 16.3 g of (3,4-dichloro phenyl) acetic acid and 12.89 g of carbonyldiimidazol. 30.48 g of expected product is obtained which is used as it is for the following Example.

EXAMPLE 12

(1S)-3-(3,4-dichlorophenyl)-1-[1-phenyl-2-(1-pyrrolidinyl)-ethyl]-2,4-piperidinedione.

The operation is carried out as in Example 2 starting with 28.6 g of the product obtained in Example 11, using 3.3 g sodium hydride. 24.74 g of desired product is obtained which is used as it is for the following example. M.p.=110°–115° C. crystallized from diethyl ether.

EXAMPLE 13

(S)-3-(3,4-dichlorophenyl)-5,6-dihydro-1-[1-phenyl-2-(1-pyrrolidinyl)-ethyl]-2-(1H)-pyridinone and its fumarate.

Stage A: (S)-2-[3-(3,4-dichlorophenyl)-2-oxo-1-[1-phenyl-2-(1-pyrrolidinyl)-ethyl]-1,2,5,6-tetrahydro-4-pyridyl]-hydrazide of 4-methyl benzenesulphonic acid.

The operation takes place as in Stage A of Example 3, starting with 30 g of the product obtained as in Example 12 and 14 g of paratoluenesulphonhydrazide. Agitation takes place for 5 hours and the acetic acid is distilled off under reduced pressure. The whole is alkalinized to pH9 with 12.5 g of sodium carbonate. After extracting with methylene chloride, drying, filtering and bringing to dryness under reduced pressure, 39 g of product is obtained and is used as it is for the following stage. $[alpha]_D$ (on purified product) +64,5°±1.5°0 (c=1% methanol).

Stage B: (S)-3-(3,4-dichlorophenyl)-5,6-dihydro-1-[1-phenyl-2-(1-pyrrolidinyl)-ethyl]-2-(1H)-pyridinone and its fumarate.

The operation takes place as in Stage B of Example 3 starting with 39 g of product obtained in Stage A above, using 6.05 g of sodium and 250 cm³ of ethylene glycol. 22.33 g of expected product is obtained in the form of the base.

Obtaining the Fumarate:

22.17 g of the above product is dissolved in 65 cm³ of hot ethanol 100 and 6.4 g of fumaric acid is added. Heating takes place at 60° C. until dissolution then the whole is cooled down and separated at 20° C., washed with iced ethanol then with ether, and 15.64 g of sought product is obtained. M.p.=162°–164° C.

Return to the Base:

6.9 g of the product obtained above is dissolved in 100 cm³ of ethyl acetate and 40 cm³ of an aqueous solution of 10% sodium carbonate. After decanting and re-extracting with ethyl acetate, drying, filtering and distilling to dryness under reduced pressure, 5.4 g of product is obtained in the form of the base which is used as it is for the following example. An analytic sample of the fumarate was prepared by recristallisation of 500 mg of the above fumarate from 4 cm³ of ethanol 100. 267 mg of pure fumarate is obtained. M.p.=162°–164° C. $[alpha]_D$ +118°±2° (c=1% methanol).

| Analysis for $C_{23}H_{24}ON_2Cl_2, C_4H_4O_4$ | | | | |
|---|---|---|---|---|
| | C % | H % | N % | Cl % |
| % calculated | 61.02 | 5.31 | 5.27 | 13.34 |
| % found | 61.0 | 5.1 | 5.2 | 13.5 |

EXAMPLE 14

(1S)-3-(3,4-dichlorophenyl)-1-[1-phenyl-2-(1-pyrrolidinyl)-ethyl]-2-piperidinone (isomer A and isomer B) and the maleate of isomer A.

First Method:

The operation is carried out as in Example 4 starting with 5.4 g of the product obtained in Example 13, using 0.6 g of 80% platinum oxide and by hydrogenating under a pressure of 1500 mbars, 400 cm³ of hydrogen is absorbed, 5.81 g of expected product is obtained which is chromatographed on silica (eluant: ethyl acetate with 2% triethylamine). 0.975 g of isomer A and 1.80 g of isomer B of the expected product are obtained.

Obtaining the Maleate:

901 mg of the crude product (isomer A) is dissolved in 6 cm³ of ethyl acetate, 251 mg of maleic acid is added and the whole is heated to 60° C. After cooling to 20° C. over 1 hour, separating, washing with ethyl acetate and with ether, 1.02 g of desired product is obtained. M.p.=140°–141° C. $[alpha]_D$ +63°5±1°5 (c=1% methanol).

| Analysis for $C_{23}H_{26}Cl_2N_2O, C_4H_4O_4$ | | | | |
|---|---|---|---|---|
| | C % | H % | N % | Cl % |
| % calculated | 60.79 | 5.67 | 5.25 | 13.29 |
| % found | 61.1 | 5.6 | 5.3 | 13.2 |

NMR CDCl₃ 300 MHz (base)

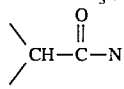    3.68 (dd, J = 7 and 9)

    6.22 (dd, S = 12 and 4.5)

H aromatic    { 7.20 (d, l) 1H
                7.25 to 7.40 (m) 7H 1.62 to 3.37    the 16 other protons.

Second Method:

3.01 g of product prepared in Example 13 is dissolved in 30 cm³ ethanol, 0.6 g of sodium borohydride is added and agitation takes place for 6 hours. 2 cm³ of water is added, the temperature is maintained at 20°–25° C., 1 cm³ of acetic acid (pH=6) is added, the solvents are eliminated under reduced pressure, the residue is taken up in an aqueous solution of 20% sodium carbonate then extracted with ethyl acetate. After drying and concentrating to dryness under reduced pressure, 3.1 g of expected product is obtained which is used as it is.

A chromatography test on silica of 615 mg of product allowed 380 mg of isomer A and 229 mg of isomer B to be obtained.

EXAMPLE 15

Fumarate of (1S)-3-(3,4-dichlorophenyl)-1-[1-phenyl-2-(1-pyrrolidinyl)-ethyl]-2-piperidinone (isomer B).

1.75 g of the product obtained in Example 14 (isomer B) is dissolved in 8 cm³ of isopropanol and 490 mg of fumaric acid is added, heating takes place until dissolution, followed by cooling to 20° C., separating, washing in isopropanol at 5° C. then with ether. 1.594 g of product is obtained which is recrystallized from 6 cm³ of ethanol 100.

1.197 g of sought product is obtained. M.p.=186°–188° C. $[alpha]_D$ +152°±3° (c=1% methanol).

NMR CDCl₃ 300 MHz
7.04 (dd) 7.27 (d)    aromatics 3.74 m    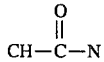

| | |
|---|---|
| 6.11 (dd, J = 10 and 6) |  CH—C$_6$H$_5$ |
| 7.25 to 7.45 (m) | 6H aromatics |
| 1.79 to 3.33 | 16 other protons. |

EXAMPLE 16

Ethyl (S)-3-((4-trifluoromethyl)-acetyl)-(1-phenyl-2-pyrrolidinyl)-ethyl)-amino) propanoate The operation is carried out as in Stage B of Example 1 using 5.31 g of 4-trifluoromethyl phenylacetic acid, 4.22 g of carbonyldiimidazol and 7.27 g of the dihydrochloride of ethyl (S)-3-[[1-phenyl-2-(1-pyrrolidinyl)-ethyl]-amino]propanoate prepared as in Stage A of Example 11 maintaining the reaction medium under agitation for 20 hours at ambient temperature.

After chromatography on silica (eluant: ethyl acetate) 9.8 g of expected product is obtained. [alpha]$_D$ +89.5°±2° (c=1% methanol).

EXAMPLE 17

(1S)-3-(4-trifluoromethyl)-1-[1-phenyl-2-(1-pyrrolidinyl)-ethyl]-2,4-piperidinedione The operation takes place as Example 2 starting with 9.42 g of the product obtained in Example 16 using 1.15 g of sodium hydride. 9.35 g of expected product is obtained which is used as it is for the following example.

EXAMPLE 18

(S)-3-(4-trifluoromethyl)-5,6-dihydro-1-[1-phenyl-2-(1-pyrrolidinyl)-ethyl]-2-(1H)-pyridinone and its fumarate Stage A: (S)-[3-(4-trifluoromethyl)-2-oxo-1-[1-phenyl-2-(1-pyrrolidinyl)-ethyl]-1,2,5,6-tetrahydro-4-pyridyl]-hydrazide of 4-methyl-benzene sulphonic acid.

The operation is carried out as in Stage A of Example 13 starting with 9.35 g of the product obtained in Example 17 ad 4.86 of p.toluene sulphonyhydrazide and 15.16 g of expected product is obtained which is used such as it for the following stage.

Stage B: (S)-3-(4-trifluoromethyl)-5,6-dihydro-1-[1-phenyl-2-(1-pyrrolidinyl)-ethyl]-2-(1H)-pyridinone and its fumarate.

The operation is carried out as in Stage B of Example 3 starting with 15.16 g of product obtained in Stage A, 2.1 g of sodium and 85 cm$^3$ of ethylene glycol. After chromatography on silica (eluant: ethyl acetate) 4.17 g of expected product is obtained in the form of the base.

Operating as in Example 13 starting with 201 mg of the base and 60 mg of fumaric acid, 116 mg of the expected fumarate is obtained. M.p.=198°–200° C. [alpha]$_D$ +93.5°±3° (c=0.5% dimethylformamide).

| Analysis for C$_{24}$H$_{25}$F$_3$N$_2$O, C$_4$H$_4$O$_4$ | | | | |
|---|---|---|---|---|
| | C % | H % | N % | F % |
| % calculated | 63.39 | 5.51 | 5.28 | 10.08 |
| % found | 63.1 | 5.4 | 5.4 | 10.7 |

EXAMPLE 19

(S)-1-[1-phenyl-2-(1-pyrrolidinyl)-ethyl]-3-(4-trifluoromethyl)-phenyl)-2-piperidinone (isomer A and isomer B) and the fumarate of isomer A 3.91 g of the base obtained in Example 18 in 40 cm$^3$ of ethanol in the presence of 0.79 g of sodium borohydride is agitated for 5 hours at ambient temperature.

Neutralization takes place by the addition of 8 cm$^3$ of an acetic acid-water mixture (1—1). The solvent is distilled off under reduced pressure, the residue is taken up with 50 cm$^3$ of ethyl acetate, 30 cm$^3$ of 20% sodium carbonate and 20 cm$^3$ of water.

The reaction medium is agitated, followed by decanting, extracting with ethyl acetate, drying, eliminating the solvents under reduced pressure and 4.15 g of crude product is obtained which is chromatographed on silica (eluant: ethyl acetate with 2% triethylamine). 2.07 g of isomer A, M.p.= 126°–128° C. and 1.2 g of B isomer are obtained.

Preparation of the Fumarate of Isomer A 1.59 g of isomer A is dissolved in 5 cm$^3$ of ethanol, 443 mg of fumaric acid is added, the solution is filtered and concentrated to dryness under reduced pressure. Crystallization is started, followed by diluting with 10 cm$^3$ of 1,2-dimethoxyethane, separating and rinsing with ether. After drying under reduced pressure at 80° C. 998 mg of crude product is collected.

After recrystallization of 953 mg of product from ethyl acetate, 528 mg of expected product is obtained. M.p.= 176°–178° C. [alpha]$_D$ +73°±2.5° (c=0.5% H$_2$O).

| Analysis for C$_{24}$H$_{27}$ON$_2$F$_3$, C$_6$H$_6$O$_6$ | | | | |
|---|---|---|---|---|
| | C % | H % | N % | F % |
| % calculated | 61.00 | 5.63 | 4.74 | 9.65 |
| % found | 60.8 | 5.6 | 4.7 | 9.9 |

EXAMPLE 20

Fumarate of (S)-1-[1-phenyl-2-(1-pyrrolidinyl)-ethyl]-3-(4-trifluoromethyl)-phenyl)-2-piperidinone (isomer A and isomer B) and the fumarate of isomer B 1.16 g of isomer B in the form of the base obtained in Example 19 is dissolved in 2 cm$^3$ of ethanol, 333 mg of fumaric acid is added and the whole is heated under reflux until complete dissolution. After cooling to ambient temperature, the crystals formed are separated, then rinsed in an ethanol-ether mixture, then ether. After drying at 80° C. under reduced pressure, 989 mg of expected product is obtained. M.p.=168°–170° C. [alpha]$_D$ +150°±3.5° (c=0.5% H$_2$O).

| Analysis for $C_{24}H_{27}F_3N_2O$, $(C_4H_4O_4)$ | | | | |
|---|---|---|---|---|
| | C % | H % | N % | F % |
| % calculated | 63.15 | 5.87 | 5.26 | 10.70 |
| % found | 62.9 | 5.8 | 5.3 | 10.6 |

EXAMPLE 21

Ethyl (S)-3-(((3,4-dichlorophenyl)-acetyl)-1-(2-methyl-1-((1-pyrrolidinyl)-methyl)-propyl)-amino) propanoate.

Stage A: Ethyl (S)-3-((2-methyl-1-(1-pyrrolidinyl)-methyl)-propyl)-amino) propanoate.

The operation is carried out as Stage A of Example 1, using 18.24 g of 2-methyl-1-((1-pyrrolidinyl)-methyl) propylamine and 15.1 cm³ of ethyl acrylate. 29 g of expected product is obtained. $[alpha]_D$ +43.5°±1.5°0 (c=1% methanol).

Stage B: Ethyl (S)-3-(((3,4-dichlorophenyl)-acetyl)-1-(2-methyl-1-((1-pyrrolidinyl)-methyl)-propyl)-amino)-propanoate.

The operation is carried out as Stage B of Example 1 starting with 28.7 g of 3,4-dichlorophenylacetic acid, 27.52 g of the product obtained in Stage A and 22.7 g of carbonyldiimidazol. 57.2 g of crude product is obtained which is purified by chromatography on silica (eluant: ethyl acetate-methanol (95-5)) and 39.2 g of expected product is obtained. $[alpha]_D$ +26.5°±1.5° (c=0.8% methanol).

Preparation of 2-methyl-1-((1-pyrrolidinyl)-methyl)-propylamine used at the start of Example 21.

Stage A: 1-[3-methyl-(S)-2-[[(phenylmethoxy)-carbonyl]-amino]-butanoyl]pyrrolidine 32.6 g of butanoic 3-methyl-(S)-2-[[(phenylmethoxy)-carbonyl]-amino], 20 g of hydroxybenzotriazol hydrated in 326 cm³ of methylene chloride are mixed together at ambient temperature, cooled to 0° C. and a chilled solution containing 30 g of dicyclohexylcarbodiimide in 128 cm³ of methylene chloride is added over 20 minutes. Agitation takes place for 1 hour at 0°/+5° C., 15 cm³ of pyrrolidine is added over 10 minutes, agitation takes place for 20 hours whilst allowing the mixture to return to ambient temperature. The whole is filtered, rinsed with methylene chloride then with ether and concentrated to dryness under reduced pressure.

After chromatography on silica (eluant: ethyl acetate with 2% triethylamine, 42.88 g of expected product is obtained which is used as it is for the following stage. $[alpha]_D$ −6°±1° (c=1% methanol).

Stage B: 1[(S)-2-amino-3-methyl-butanoyl]-pyrrolidine

A mixture containing 42.88 g of the product obtained in Stage A in 429 cm³ of ethanol and 17 cm³ of hydrochloric acid in the presence of 4.22 g of activated charcoal with 10% of palladium has a stream of hydrogen under 1880 mbars passed through it for 3 hours. After filtering, the filtrate is concentrated under reduced pressure. Crystallization is started, the residue is taken up with 50 cm³ of ethyl acetate, the expected product crystals are separated in the form of the hydrochloride, they are dissolved in 25 cm³ of water and 25 cm³ of caustic soda lye is added. Extraction takes place with methylene chloride, followed by drying and eliminating the solvent under reduced pressure. 19.79 g of expected product is obtained which is used as it is for the following stage. $[alpha]_D$ +35.5°±2.5° (c=0.3% methanol).

Stage C: 2-methyl-1-((1-pyrrolidinyl)-methyl) propylamine 8.2 g of lithium aluminium hydride is introduced into 400 cm³ of tetrahydrofuran cooled to −10° C., then a solution containing 19.79 g of product obtained in Stage B in 100 cm³ of tetrahydrofuran, cooled to −5°/−8° C., is added over 20 minutes. Agitation takes place for 2 hours and 30 minutes maintaining the temperature at 8°/+5° C., and 30 cm³ of an aqueous solution of 20% sodium carbonate is added then agitation takes place for 20 hours at ambient temperature.

After filtering and concentrating the filtrate to dryness under reduced pressure 17.37 g of expected product is collected which is used as it is for the continuation of the synthesis. $[alpha]_D$ +45.5°±1.5° (c=1% methanol).

EXAMPLE 22

(S)-3-(3,4-dichlorophenyl)-1-(2-methyl-1-((1-pyrrolidinyl)-methyl)-propyl)-2,4-piperidinedione The operation is carried out as in Example 2 starting with 16.71 g of the product obtained in Example 21 using 2.76 g of sodium hydride. 13.37 g of expected product is obtained which is used as it is for the following example. $[alpha]_D$ +23°±1.5° (c=1% methanol).

EXAMPLE 23

(S)-3-(3,4-dichlorophenyl)-5,6-dihydro-1-(2-methyl-1-((1-pyrrolidinyl)-methyl)-propyl)-2-(1H)-piperidinone.

Stage A: (S)-2-[3-(3,4-dichlorophenyl)-2-oxo-1-(2-methyl-1-((1-pyrrolidinyl)-methyl)-propyl)-1,2,5,6-tetrahydro-4-pyridyl]-hydrazide of 4-methyl benzenesulfonic acid.

The operation is carried out as in Stage A of Example 13 starting with 11.85 g of the product obtained in Example 23 and 7.70 g of p.toluenesulphonidrazide and 18.09 g of expected product is obtained which is used as it is for the following stage.

Stage B: (S)-3-(3,4-dichlorophenyl)-5,6-dihydro-1-(2-methyl-1-((1-pyrrolidinyl)-methyl)-propyl)-2-(1H)-piperidinone The operation is carried out as Stage B of Example 3 starting with 18.09 g of product obtained in Stage A, 3.15 g of sodium and 130 cm³ of ethylene glycol. After chromatography on silica (eluant: ethyl acetate with 2% triethylamine), 11.24 g of expected product is obtained in the form of the base. Operating as in Example 13 starting with 11.24 g of base and 3.57 g of fumaric acid, 17 g of the fumarate is obtained. M.p.=166°–168° C.

Return to the Base 17 g of the product obtained above is taken up in 100 cm³ of ethyl acetate and 20 cm³ of water and 2.5 g of sodium carbonate are slowly added. After agitating, decanting, extracting with ethyl acetate, washing with salt water, drying and eliminating the solvents under reduced pressure, 5.54 g of expected product is obtained in the form on the base. $[alpha]_D$ +7.5°±1° (c=1% methanol).

EXAMPLE 24

(S)-3-(3,4-dichlorophenyl)-1-(2-methyl-1-((1 pyrrolidinyl)-methyl)-propyl)-2-piperidinone isomer A, isomer B and the maleate of isomer A The operation is carried out as in Example 19 starting with 3.25 g of the base obtained in Example 23 and 0.77 g of sodium borohydride and 3.17 g of crude product is obtained. After chromatography, 1.44 g of isomer A and 1.37 g of isomer B are obtained.
Preparation of the Maleate of Isomer A:

1.55 g of isomer A obtained as previously is dissolved in 5 cm³ of ethanol, 515 mg of maleic acid in solution in 5 cm³ of ethanol is added, crystallization is started, followed by separating, rinsing with ethanol then with ether and 1.85 g of expected product is obtained. [alpha]$_D$ +81°±2° (c=0.5% dimethylformamide).

| Analysis for $C_{20}H_{28}N_2OCl_2, C_4H_4O_4$ | | | | |
|---|---|---|---|---|
| | C % | H % | N % | Cl % |
| % calculated | 57.72 | 6.46 | 5.61 | 14.20 |
| % found | 58.0 | 6.5 | 5.6 | 14.1 |

EXAMPLE 25

Maleate of (S)-3-(3,4-dichlorophenyl)-1-(2-methyl-1-((1-pyrrolidinyl)-methyl)-propyl)-2-piperidinone isomer B 1.46 g of isomer B obtained in Example 24 is dissolved hot in a solution containing 486 mg of maleic acid in 5 cm³ of ethyl acetate.

Crystallization is started, the crystals formed are separated, rinsed with ethyl acetate then with ether and then dried under reduced pressure at 80° C. 1.77 g of the expected maleate is obtained. [alpha]$_D$ −60.5°±2.5° (c=0.5% dimethylformamide).

| Analysis for $C_{20}H_{28}N_2Cl_2O, C_4H_4O_4$ | | | | |
|---|---|---|---|---|
| | C % | H % | N % | Cl % |
| % calculated | 57.72 | 6.46 | 5.61 | 14.20 |
| % found | 57.7 | 6.4 | 5.4 | 13.8 |

EXAMPE 26

Ethyl (S)-3-phenyl-acetyl-(1-phenyl-2-(1-pyrrolidinyl)-ethyl-amino) propanoate

The operation takes place as in Stage B of Example 1 using 3.54 g of phenyl acetic acid, 4.22 g of carbonyldiimidazol and 7.27 g of dihydrochloride of ethyl (S)-3-((1-phenyl-2-(1-pyrrolidinyl)-ethyl)-amino) propanoate prepared as in Stage A of Example 11 by maintaining the reaction medium under agitation for 20 hours at ambient temperature.

After chromatography on silica (eluant: ethyl acetate 8.15 g of expected product is obtained. [alpha]$_D$ +96.5°±2° (c=1% methanol).

EXAMPLE 27

(S)-3-phenyl-1-(1-phenyl-2-(1-pyrrolidinyl) ethyl-2,4-piperidine dione

The operation is carried out as in Example 2 starting with 7.955 g of the product obtained in Example 26 and 1.12 g of sodium hydride.

6.70 g of expected product is obtained which is used as it is for the following example.

EXAMPLE 28

(S)-3-phenyl-5,6-dihydro-1-(1-phenyl-2-(1-pyrrolidinyl)-ethyl)-2-(1H)-pyridinone Stage A: (S)-3-phenyl-2-oxo-1-(1-phenyl-2-(1-pyrrolidinyl) ethyl)-1,2,5,6-tetrahydro-4-pyridyl)-hydrazide of 4-methyl-benzenesulphonic acid.

The operation is carried out as in Stage A of Example 13 starting with 6,7 g of the product obtained in Example 27 and 4.50 g of p.toluene sulphonyhydrazide and 10.40 g of expected product is obtained which is used as it is for the following stage.

STAGE: (S)-3-phenyl-5,6-dihydro-1-(1-phenyl-2-)1-pyrrolidinyl)-ethyl)-2-(1H)-pyridinone The operation is carried out as in Stage B of Example 3 starting with 10.40 g of product obtained in Stage A, 2.0 g of sodium and 80 cm³ of ethylene glycol. After crystallization from isopropyl ether 2.75 g of expected product is obtained in the form of the base.
[alpha]$_D$+177°±3°(c=1% methanol).

EXAMPLE 29:
(S)-3-phenyl-1-(1-phenyl-2-(1-pyrrolidinyl)-ethyl)-2-piperidinone (isomer A, isomer B and the fumarate of isomer A)

The operation is carried out as in Example 19 staring with 2.66 g of product obtained in Example 28 and 0.62 g of sodium borohydride. 2.7 g of crude product is obtained. After chromatography, 1.59 g of isomer A and 1.05 g of isomer B are collected.

Preparation of the fumarate of isomer A

The operation is carried out as in Example 19 starting with 1.55 g of isomer A prepared above and 568 mg of fumaric acid. 1.92 g of the expected fumarate is obtained. M.p.= 191°–193° C.
[alpha]$_D$+97.5°±2°(c=1% dimethylformamide).

| Analysis for $C_{23}H_{28}N_2O, C_4H_4O_4$ | | | |
|---|---|---|---|
| | C % | H % | N % |
| % calculated | 69.81 | 6.94 | 6.03 |
| % found | 69.7 | 7.0 | 6.0 |

EXAMPLE 30: Fumarate of (S)-3-phenyl-1-(1-phenyl-2-(1-pyrrolidinyl)-ethyl)-2-piperidinone of isomer B The operation is carried out as in Example 20 starting with 9.81 mg of isomer B prepared in Example 29 and 325 mg of fumaric acid. 1.07 g of the expected fumarate is obtained. M.p.=200°–202° C.
[alpha]$_D$+116°±2°(c=1% dimethylformamide).

| Analysis for $C_{23}H_{28}ON_2, C_4H_4O_4$ | | | |
|---|---|---|---|
| | C % | H % | N % |
| % calculated | 69.81 | 6.94 | 6.03 |
| % found | 69.5 | 7.0 | 6.0 |

EXAMPLE 31: Ethyl (S)-3-((benzo (b) thien-4-yl)-acetyl)-1 -(1-phenyl-2-(1-pyrrolidinyl)-ethyl)-amino) propanoate The operation is carried out as in Stage B of Example 1 using 5 g of 4-thianaphthene acetic acid, 4.22 g of carbonyldiimidazol and 7.27 g of the dihydrochloride of ethyl (S)-3-[[1-phenyl-2-(1-pyrrolidinyl)-ethyl]-amino] propanoate prepared as in Stage A in Example 11 by maintaining the reaction medium under agitation for 20 hours at ambient temperature.

After chromatography on silica (eluant: ethyl acetate) 9.66 g of expected product is obtained.
[alpha]$_D$+79°±2°(c=1% methanol).

EXAMPLE 32: (S)-3-(benzo (b) thien-4-yl)-1-(1-phenyl-2-(1 -pyrrolidinyl)-ethyl)-2,4-piperidinedione The operation is carried out as in Example 2 starting with 9.47 g of the product obtained in Example 31 using 1.15 g of sodium hydride. 10.45 g of expected product is obtained which is used as it is for the following example.

EXAMPLE 33: (S)-3-(benzo (b) thien-4-yl)-5,6-dihydro-1-(1 -phenyl-2-(1-pyrrolidinyl)-ethyl)-2-(1H-pyridinone and its fumarate

STAGE A: (S)-2-[3-(benzo (b) thien-4-yl)-2-oxo-1-[1-phenyl-2-(1-pyrrolidinyl)-ethyl]-1,2,5,6-tetrahydro 4-pyridyl]-hydrazide of 4-methyl benzenesulphonic acid.

The operation is carried out as in Stage A of Example 13 starting with 10.45 g of the product obtained in Example 32 and 4.86 g of p.toluene sulphonyhdrazide and 15.03 g of expected product is obtained which is used as it is for the following stage.

STAGE B: (S)-3-(benzo (b) thien-4-yl)-5,6-dihydro-1-(1 -phenyl-2-(1-pyrrolidinyl)-ethyl)-2-(1H-pyridinone and its fumarate.

The operation is carried out as in Stage B of Example 3 starting with 15.03 g of the product obtained in Stage A, 2.16 g of sodium and 85 cm$^3$ of ethylene glycol. After chromatography on silica (eluant: ethyl acetate) 8.29 g of expected product is obtained in the form of the base. By operating as in Example 13 starting with 8.26 g of the base and 2.5 g of fumaric acid, 6.82 g of the expected fumarate is obtained. M.p.=194°–195° C.

Return to the base 5.66 g of the above fumarate is taken up in 20 cm$^3$ of water and 30 cm$^3$ of an aqueous solution of 20% sodium carbonate and 100 cm$^3$ of ethyl acetate are added. Agitation takes place, followed by decanting, extracting with ethyl acetate, drying and concentrating to dryness under reduced pressure. 4.93 g of expected product is collected in the form of the base, which is used as it is for the following example.

EXAMPLE 34: (S)-3-(benzo (b) thien-4-yl)-1-(1-phenyl-2-(1 -pyrrolidinyl)-ethyl)-2-piperidinone (isomer A, isomer B and the fumarate of isomer A)

The operation is carried out as in Example 19 starting with 4.93 g of product obtained in Example 33 and 3 times 1 g of sodium borohydride. 5.23 g of crude product is obtained. After chromatography, 2.64 g of isomer A and 2.07 g of isomer are collected.

Preparation of the fumarate of isomer A

The operation is carried out as in Example 19, starting with 2.55 g of isomer A prepared above and 823 mg of fumaric acid. 2.79 g of the expected fumarate is obtained. M.p.=234°–238° C.
[alpha]$_D$+110°±2° (c=1% dimethylformamide).

| Analysis for $C_{24}H_{28}N_2OS, C_4H_4O_4$ | | | |
|---|---|---|---|
| C % | H % | N % | S % |
| % calculated 66.90 | 6.19 | 5.38 | 6.16 |
| % found 67.0 | 6.2 | 5.3 | 6.2 |

EXAMPLE 35: Fumarate of (S)-3-(benzo (b) thien-4-yl)-1-(1-phenyl-2-(1-pyrrolidinyl)-ethyl)-2-piperidinone (isomer B)

The operation is carried out as in Example 20 starting with 1.90 g of isomer B prepared in Example 34 and 628 mg of fumaric acid. 1.38 g of the expected fumarate is obtained. M.p.=195°–197° C.
$[alpha]_D+110°\pm2°$ (c=1% dimethylformamide).

| Analysis for $C_{24}H_{28}ON_2S$, $C_4H_4O_4$ | | | | |
|---|---|---|---|---|
| | C % | H % | N % | S % |
| % calculated | 66.90 | 6.19 | 5.38 | 6.16 |
| % found | 67.0 | 6.2 | 5.3 | 6.2 |

EXAMPLE 36:
(S)-3-(3,4-dichlorophenyl)-3-methyl-1-(1-phenyl-2-(1-pyrrolidinyl)-ethyl)-2-piperidinone (isomer A, isomer B and the maleate of isomer A)

2.67 g of crude (S)-3-(3,4-dichlorophenyl)-1-(1-phenyl-2-(1-pyrrolidinyl)-ethyl)-2-piperidinone obtained in Example 14 in 40 cm³ of tetrahydrofuran is cooled to −20° C. and 1.16 g of potassium terbutylate is added then the solution is agitated for 1 hour at −8°±2° C. After cooling to −15° C., 0.6 cm³ of methyl iodide is added then agitation takes place for 2 hours and 30 minutes at −7°/−10° C. The temperature is allowed to return to 0°0 C., 50 cm³ of chilled water is added, extraction takes place with ethyl acetate, followed by drying and concentrating to dryness under reduced pressure. 2.83 g of crude product is obtained in the form of the base which is chromatographed on silica (eluant: ethyl acetate—n-hexane (9-1) then ethyl acetate with 1% of triethylamine). 0.996 g of isomer A and 1.307 g of isomer B are obtained.

Maleate of isomer A 947 mg of the above isomer A and 304 mg of maleic acid are dissolved in 4 cm³ of ethyl acetate whilst warning slightly After filtering, 3 cm³ of ethyl ether is added to the filtrate, crystallization is started, the crystals are separated, then rinsed with ethyl acetate and with ether, dried at 70° C. under reduced pressure and 823 mg of the expected maleate is collected. M.p.=136°–138° C.
$[alpha]_D+60.5°\pm1.5°$ (c=1% methanol).

| Analysis for $C_{24}H_{28}ON_2Cl_2$, $C_4H_4O_4$ | | | | |
|---|---|---|---|---|
| | C % | H % | N % | Cl % |
| % calculated | 61.43 | 5.89 | 5.12 | 12.95 |
| % found | 61.6 | 6.0 | 5.1 | 12.8 |

EXAMPLE 37: Fumarate of (S)-3-(3,4-dichlorophenyl)-3-methyl-1-(1-phenyl-2-(1-pyrrolidinyl)-ethyl)-2-piperidinone (isomer B)

1.24 g of isomer B obtained in Example 36 is dissolved in 5 cm³ of ethano whilst cooling, 370 mg of fumaric acid is added and heating under reflux takes place until total dissolution. After cooling, crystallization is started, the crystals are separated, rinsed with ethanol then with ether, dried at 70° C. under reduced pressure and 1.25 g of the expected fumarate is collected. M.p.=175°–176° C.
$[alpha]_d+125°\pm2°$ (c=1% methanol).

| Analysis for $C_{24}H_{28}N_2Cl_2O$, $C_4H_4O_4$ | | | | |
|---|---|---|---|---|
| | C % | H % | N % | Cl % |
| % calculated | 61.43 | 5.89 | 5.12 | 12.95 |
| % found | 61.5 | 5.8 | 5.0 | 12.8 |

EXAMPLE 38:
(1S)-3-(3,4-dichlorophenyl)-3-ethyl-1-(1-phenyl-2-(1-pyrrolidinyl)-ethyl)-2-piperidinone (isomer B, isomer A and the methane sulphonate of isomer B)

The operation is carried out as in Example 36 starting with 2 g of the product obtained in Example 14, 0.87 g of potassium terbutylate and 0.6 cm³ of ethyl iodide. 2.1 g of crude product is obtained in the form of the base which is chromatographed on silica (eluant: ethyl acetate-methylene chloride (85-15)).

1.05 g of isomer A and 0.87 g of isomer B are obtained.

A paste is made of 0.87 g of isomer B in 4 cm³ of a mixture of isopropyl—ether n-hexane (1-1), the crystallized product is separated, dried and 0.567 g of expected isomer B product is obtained. M.p.=113°–114° C.

Preparation of the methane sulphonate of isomer B 542 mg of isomer B is dissolved, at ambient temperature, in 2 cm³ of ethanol and 0.7 cm³ of an ethanolic solution of 2M methane sulphonic acid, crystallization is started, followed by diluting with 1 cm³ of ethyl ether, separating and drying the crystals under reduced pressure at 70° C. 268 mg of expected mathane sulphonate is obtained. M.p.=207°–209° C.
$[alpha]_D+107°\pm2°$ (c=1% methanol).

| Analysis for $C_{26}H_{34}N_2Cl_2O_4S$ | | | | | |
|---|---|---|---|---|---|
| | C % | H % | N % | S % | Cl % |
| % calculated | 57.67 | 6.33 | 5.17 | 5.92 | 13.09 |
| % found | 57.7 | 6.4 | 5.1 | 5.9 | 13.4 |

EXAMPLE 39: Fumarate of (1S)-3-(3,4-dichlorophenyl)-3-ethyl-1-phenyl-2-(1-pyrrolidinyl)-ethyl)-2-piperidinone (isomer A)

A paste is made with 1.05 g of the isomer obtained in Example 38 in 4 cm³ of isopropyl ether at ambient temperature, the crystals are separated, rinsed with n-hexane, and dried under reduced pressure. 599 mg of crystallized product is collected in the form of the base. M.p.=123°–124° C. The operation is carried out as in Example 37, starting with 587 mg of the base and 168 mg of fumaric acid. 559 mg of the expected fumarate is obtained. M.p.=148°–150° C. $[alpha]_D+46.5°\pm1.5°$ (c=1% methanol).

| Analysis for $C_{25}H_{30}N_2OCl_2, C_4H_4O_4$ | | | | |
| --- | --- | --- | --- | --- |
|  | C % | H % | N % | Cl % |
| % calculated | 62.02 | 6.10 | 4.99 | 12.63 |
| % found | 61.9 | 6.1 | 4.8 | 12.9 |

EXAMPLE 40: (1S-3-)3,4-dichlorophenyl)-3-(phenylmethyl)-1-(1-phenyl-2-(1-pyrrolidinyl)-ethyl)-2-piperidinone (isomer B, isomer A and the fumarate of isomer B)

The operation is carried out as in Example 36 starting with 2.76 g of product obtained in Example 14, 0.98 g of potassium terbutylate and 1.2 cm³ of benzyl bromide. 3.22 g of expected product is obtained in the form of the base. After chromatography on silica (eluant: ethyl acetate—methylene chloride (75-15)), 668 mg of isomer A and 533 mg of isomer B are obtained.

Preparation of the fumarate of isomer B

The operation is carried out as in Example 37 starting with 455 mg of isomer B dissolved in 5 cm³ of isopropanol and 110 mg of fumaric acid. 350 mg of the expected fumarate is obtained. M.p.=195°–197° C.
$[alpha]_D+57.5°\pm1.5°$ (c=1% dimethylformamide)

| Analysis for $C_{30}H_{32}N_2Cl_2O, C_4H_4O_4$ | | | | |
| --- | --- | --- | --- | --- |
|  | C % | H % | N % | Cl % |
| % calculated | 65.19 | 5.82 | 4.49 | 11.37 |
| % found | 65.3 | 5.9 | 4.5 | 11.3 |

EXAMPLE 41: (1S)-3-(3,4-dichlorophenyl)-3-(phenylmethyl)-1-(1-phenyl-2-(1-pyrrolidinyl)-ethyl)-2-piperidinone hydrochloride (isomer A)

462 mg of isomer A base obtained in Example 40 is dissolved in 4.5 cm³ of ethanol at ambient temperature and 0.5 cm³ of a 6.6N ethanolic solution of hydrogen chloride is added. Crystallization is started, followed by separating and drying the crystals at 80°0 C. under reduced pressure and 340 mg of the expected hydrochloride is collected. M.p.=206°–208° C.

$[alpha]_D+41°\pm1.5°$ (c=1% dimethylformamide)

| Analysis for $C_{30}H_{33}N_2Cl_3O$ | | | | |
| --- | --- | --- | --- | --- |
|  | C % | H % | N % | Cl % |
| % calculated | 66.24 | 6.11 | 5.15 | 19.55 |
| % found | 66.0 | 6.2 | 5.1 | 19.2 |

EXAMPLE 42: (1S)-3-(3,4-dichlorophenyl)-1-(1-phenyl-2-(1-pyrrolidinyl)-ethyl)-3-(2-propenyl)-2-piperidinone (isomer A, isomer B and the methanesulphonate of isomer A)

The operation is carried out as in Example 36 starting with 2.01 g of the product obtained in Example 14, 0.9 g of potassium terbutylate and 0.65 cm³ of allyl bromide. 2.28 g of expected crude product is obtained in the form of the base. After chromatography on silica (eluant: ethyl acetate—methylene chloride—n-hexane (3-4-3)) 868 mg of isomer A and 940 mg of isomer B are obtained.

Preparation of the methanesulphonate

The operation is carried out as in Example 38 starting with 806 mg of isomer A and 1 cm³ of an (approx. 2M) ethanolic solution of methane sulphonic acid and 628 mg of the expected methanesulphonate is obtained. M.p.=171°–172°0 C.
$[alpha]_D+41°\cong1.5°$ (c=1% dimethylformamide)

| Analysis for $C_{27}H_{34}O_4N_2Cl_2S$ | | | | | |
| --- | --- | --- | --- | --- | --- |
|  | C % | H % | N % | S % | Cl % |
| % calculated | 58.58 | 6.19 | 5.06 | 5.79 | 12.81 |
| % found | 58.7 | 6.3 | 5.2 | 5.7 | 12.8 |

EXAMPLE 43: (1S-3-(3,4-dichlorophenyl)-1-(1-phenyl-2-(1-pyrrolidinyl)-ethyl)-3-(2-propenyl)-2-piperidinone methanesulphonate (isomer B)

The operation is carried out as in Example 38 starting with 913 mg of isomer B, obtained in Example 42 and 1.2 cm³ of a (2M) ethanolic solution of methane sulphonic acid and 780 mg of the expected methanesulphonate is obtained. M.p.= 239°–241° C.
$[alpha]_D+92°\pm2°$ (c=1% dimethylformamide)

| Analysis for $C_{27}H_{34}O_4N_2Cl_2S$ | | | | | |
| --- | --- | --- | --- | --- | --- |
|  | C % | H % | N % | S % | Cl % |
| % calculated | 58.58 | 6.19 | 5.06 | 5.79 | 12.81 |
| % found | 58.9 | 6.3 | 5.1 | 5.8 | 12.6 |

Example of pharmaceutical composition

EXAMPLE 44

Tablets corresponding to the following formula were prepared:

product of Example 5 . . . 200 mg excipient sufficient quantity for . . . 800 mg (detail of excipient: lactose, talc, starch, magnesium stearate).

EXAMPLE 45

An injectable solute (intra-muscular route) was prepared corresponding to the following formula:

product of Example 5 . . . 50 mg sterile solvent sufficient quantity for . . . 5 cm³.

PHARMACOLOGICAL STUDY OF THE PRODUCT

1) Bonding to the opiated K receptor in vitro.

Membrane samples preserved at −30° C. (optionally for approximately 30 days) are used and prepared from guinea pig brains.

These samples are put in suspension in Tris pH 7.7 buffer. Fractions of 2 cm³ are distributed in hemolysis tubes and 1 nM of 9³H-ethylketocyclazocin and the product to be studied are added. The product is first tested at $5\times10^{-6}$M (in triplicate). When the test product displaces more than 50% of the radioactivity linked specifically to the receptor, it is tested again according to a range of 7 doses so as to determine the dose that inhibits 50 % of the radioactivity linked specidically to the receptor. Thus the 50% inhibiting concentration is determined.

The non-specific bond is determined by the addition of known product under the name U-50488 H (Laahti et al. 1982, Life Sci. 31, 2257) at $10^{-5}$M (in triplicate). After incubating at 25° C. for 40 minutes, returning to the water bath at 0°0 C. for 5 minutes, filtering under vacuum, rinsing with Tris pH 7.7 buffer, theradioactivity is counted in the presence of Trition scintillator.

The result is expressed directly as 50% inhibiting concentration ($IC_{50}$), namely as the concentration of studied product expressed in nM, necessary to displace 50% of the radioactivity specifically fixed on the studied receptor.

| Product of Example | $IC_{50}$ in nM |
|---|---|
| 8 | 9 |
| 7 | 0.2 |
| 4 | 22 |

2) Anti-arythmic action in the rat.

Male rats weighing 300–350 g anaesthetised by interperitonal route using 1.20 g/kg of urethane are tracheotomized and subjected to artificial respiration (40–50 insufflations of 3 ml/minute).

Needles are implanted subcutaneously so as to record the rats' electrocardiogram on the DII derivation signal.

The test products are administered by intravenous route. Five minutes after administration of the product, the jugular vein is perfused with aconitine at the rate of 10 micrograms/mn and the time taken for the appearance of cardiac rhythm disorders is noted.

The results are expressed as a percentage of the increase in the time taken for cardiac rhythm disorders to appear relative to the controls and according to the dose of the test product.

The results in the table hereafter show that some of the products of the present Application are endowed with good anti-arythmic properties.

| Product of Example | Dose mg/kg | Percentage increase in time |
|---|---|---|
| 4 | 5 | 48% |
|   | 2.5 | 23% |
| 3 | 5 | 55% |
|   | 2.5 | 52% |
| 5 | 5 | 33% |
|   | 2.5 | 26% |

What we claim is:

1. A compound selected from the group consisting of all possible racemic, enantioneric and diastereoisomeric forms of a compound of a formula

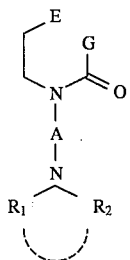

wherein E and G together form a group consisting of a)

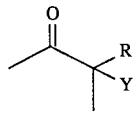

or, if appropriate,

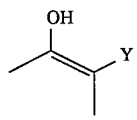

its tautomer

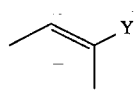

and

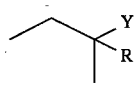

or E is —COOR₃ and G is

R is selected from the group consisting of hydrogen, alkyl of 1 to 6 carbon atoms, alkenyl or alkynyl of 2 to 6 carbon atoms optionally substituted with carbocyclic aryl selected from the group consisting of phenyl, naphthyl and indenyl optionally substituted with at least one member of the group consisting of —OH, —CF₃, alkoxy of 1to 6 carbon atoms, —NO₂, —CN, NH₂, free and esterified carboxy, acyl selected from the group consisting of formyl, acetyl, propionyl and benzoyl, alkylamino and dialkylamino of 1 to 6 carbon atoms, acyloxy selected from the group consisting of formyloxy, acetyloxy, propionyloxy and benzoyloxy, carbamoyl and halogen, Y is selected from the group consisting of disubstituted phenyl and optionally substituted naphthyl or indenyl, wherein the substitutents are independently selected from the group consisting of halogen, hydroxy, alkyl, alkynyl and alkenyl of up to 6 carbon atoms, alkoxy of 1 to 6 carbon atoms, halo alkylthio of 1 to 6 carbon atoms, mono or dialkylamino of 1 to 6 carbon atoms, optionally esterified carboxy, haloalkyl of 1 to 6 carbon atoms, haloalkoxy of 1 to 6 carbon atoms, lower alkanoyl of up to 7 carbon atoms, lower alkanoylamido, carbamoyl, phenyl and benzoyl, $R_3$ is hydrogen or alkyl of 1 to 4 carbon atoms, A is

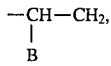

B is selected from the group consisting of hydrogen, phenyl optinally substituted with at least one member of the group consisting of halogen, —OH, —CN, $NO_2$, alkyl and alkoxy of 1 to 5 carbon atoms, $R_1$ and $R_2$ together with the nitrogen to which they are attached form pyrrolidino or piperidino and their non-toxic, pharmaceutically acceptable salts with acids and bases.

2. A compound of claim 1 having the formula

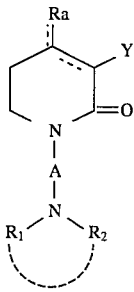

in which the group:

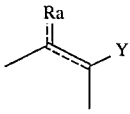

is a), b) or c) of claim 1 and A, $R_1$ and $R_2$ have the definition of claim 1.

3. A compound of claim 1 wherein E an G are a), b) or c) of claim 1 and Y has the definition of claim 1.

4. A compound of claim 1 of the formula

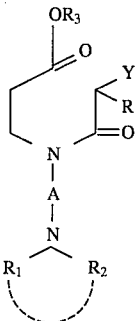

wherein R, $R_1$, $R_2$, $R_3$ A and Y have the definition of claim 1.

5. A compound of claim 1 wherein R is alkyl, alkenyl or alkynyl substituted with optionally substituted phenyl.

6. A compound of claim 1 wherein R is selected from the group consisting of hydrogen, alkyl of 1 to 6 carbon atoms, alkenyl and alkynyl of 2 to 6 carbon atoms and benzyl, Y is disubstituted phenyl substituted with members independently selected from the group consisting of halogen, alkoxy of 1 to 6 carbon atoms and —$CF_3$, B is phenyl or alkyl of 1 to 6 carbon atoms and $R_1$ and $R_2$ together with the nitrogen to which they are attached form pyrrolidinyl.

7. A compound of claim 1 selected from the group consisting of

Ethyl (S)-3-[[3,4-dichlorophenyl)-acetyl]-[1-phenyl-2-(1-pyrrolidinyl)-ethyl]-amino]-propanoate;

(1S)-3-(3,4-dichlorophenyl)-1-[1-phenyl-2-(1-pyrrolidinyl)-ethyl]-2,4-piperidinendione;

(S)-3-)3,4-dichlorophenyl)-5,6-dihydro-1-[1-phenyl-2-(1-pyrrolidinyl)-ethyl]-2-(1H-pyridinone;

(1S)-3-(3,4-dichlorophenyl)-1-[1-phenyl-2-(1-pyrrolidinyl)-ethyl]-2-piperidinone (isomer A and isomer B); and (1S)-3-(3,4-dichlorophenyl)-1-[1-phenyl-2-(1-pyrrolidinyl)-ethyl]-2-piperidinone (isomer B) and their non-toxic, pharmaceutically acceptable acid addition salts.

8. A central analgesic composition comprising a central analgesically effective amount of a compound of claim 1 and an inert pharmaceutical carrier.

9. A composition wherein the active compound is that of claim 2.

10. A method of relieving pain in warm-blooded animals comprising administering to warm-blooded animals a central analgesically effective amount of compound of claim 1.

* * * * *